United States Patent
Itoi

(10) Patent No.: US 10,586,927 B2
(45) Date of Patent: Mar. 10, 2020

(54) ORGANIC ELECTROLUMINESCENT MATERIAL AND ORGANIC ELECTROLUMINESCENT DEVICE INCLUDING THE SAME

(71) Applicant: SAMSUNG DISPLAY CO., LTD., Yongin-si, Gyeonggi-do (KR)

(72) Inventor: Hiroaki Itoi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 417 days.

(21) Appl. No.: 14/857,706

(22) Filed: Sep. 17, 2015

(65) Prior Publication Data
US 2016/0111653 A1    Apr. 21, 2016

(30) Foreign Application Priority Data

Oct. 21, 2014 (JP) ................. 2014-214447

(51) Int. Cl.

| | |
|---|---|
| *H01L 51/54* | (2006.01) |
| *C09K 11/06* | (2006.01) |
| *H01L 51/00* | (2006.01) |
| *C07D 333/76* | (2006.01) |
| *C07D 307/91* | (2006.01) |
| *C07C 211/60* | (2006.01) |
| *C07F 7/08* | (2006.01) |
| *H01L 51/50* | (2006.01) |

(52) U.S. Cl.
CPC ........ *H01L 51/0061* (2013.01); *C07C 211/60* (2013.01); *C07D 307/91* (2013.01); *C07D 333/76* (2013.01); *C07F 7/0816* (2013.01); *H01L 51/006* (2013.01); *H01L 51/0067* (2013.01); *C07C 2603/18* (2017.05); *H01L 51/0058* (2013.01); *H01L 51/0072* (2013.01); *H01L 51/0073* (2013.01); *H01L 51/0074* (2013.01); *H01L 51/0081* (2013.01); *H01L 51/0094* (2013.01); *H01L 51/5056* (2013.01); *H01L 2251/308* (2013.01)

(58) Field of Classification Search
CPC . C07C 2603/18; C07C 211/60; C07D 209/82; C07D 307/91; C07D 333/76; C07F 7/0816; H01L 51/0032; H01L 51/005; H01L 51/006; H01L 51/0058; H01L 51/0061; H01L 51/0067; H01L 51/0071; H01L 51/0072; H01L 51/0073; H01L 51/0074; H01L 51/0081; H01L 51/0094; H01L 51/50; H01L 51/5012; H01L 51/5016; H01L 51/5056
USPC ....... 428/690, 691, 917, 411.4, 336; 427/58, 427/66; 313/500–512; 257/40, 88–104; 252/301.16–301.35
See application file for complete search history.

(56) References Cited

U.S. PATENT DOCUMENTS

| | | |
|---|---|---|
| 7,998,597 B2 | 8/2011 | Saitoh et al. |
| 2007/0096639 A1 | 5/2007 | Nakashima et al. |
| 2011/0215308 A1* | 9/2011 | Im .......................... H01L 51/006 257/40 |
| 2013/0207046 A1 | 8/2013 | Pflumm et al. |
| 2013/0234118 A1* | 9/2013 | Kwon ................... H01L 51/006 257/40 |
| 2013/0264558 A1 | 10/2013 | Matsuki et al. |
| 2014/0167003 A1* | 6/2014 | Kato ................... H01L 51/0059 257/40 |

FOREIGN PATENT DOCUMENTS

| | | |
|---|---|---|
| EP | 1 834 945 A1 | 9/2007 |
| JP | 2007091719 A * | 4/2007 |
| JP | 2007-137873 A | 6/2007 |

(Continued)

OTHER PUBLICATIONS

Machine translation of JP2007-091719. Year of publication: 2007.*

(Continued)

*Primary Examiner* — Andrew K Bohaty
(74) *Attorney, Agent, or Firm* — Lewis Roca Rothgerber Christie LLP

(57) ABSTRACT

A material for an organic electroluminescent device is represented by the following General Formula (1). The organic electroluminescent device may be driven at a low voltage and may have high emission efficiency and long life.

General Formula (1)

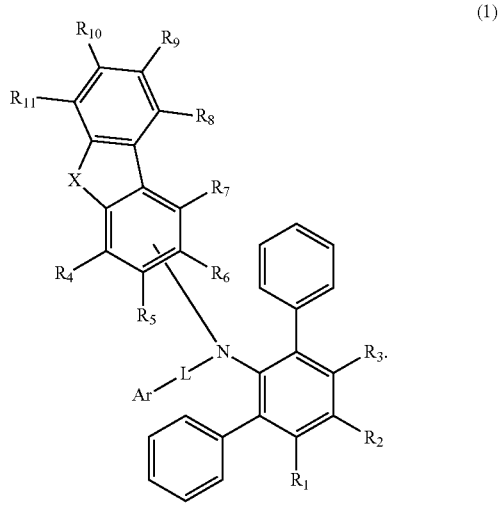

10 Claims, 1 Drawing Sheet

(56) References Cited

FOREIGN PATENT DOCUMENTS

| | | | |
|---|---|---|---|
| JP | 2009-29726 A | 2/2009 | |
| JP | 2009-267255 A | 11/2009 | |
| JP | 2011001349 A * | 1/2011 | |
| JP | 5040216 B2 | 10/2012 | |
| JP | 2013-544757 A | 12/2013 | |
| KR | 10-2012-0133145 | 12/2012 | |
| KR | 10-2016-0045019 | 4/2016 | |
| WO | WO-2010052885 A1 * | 5/2010 | ............ C07C 15/28 |
| WO | WO-2012015265 A1 * | 2/2012 | ........... C07C 211/61 |
| WO | WO 2012/090806 A1 | 7/2012 | |
| WO | WO 2013/087142 A1 | 6/2013 | |
| WO | WO 2014/050982 A1 | 4/2014 | |

OTHER PUBLICATIONS

Machine translation of JP2011-001349. (Year: 2011).*
Machine translation of WO 2010/052885. (Year: 2010).*
Abstract of Japanese Patent Publication No. 2007-091719, Apr. 12, 2007 Corresponding to Japanese Patent No. 5040216 B2, Oct. 3, 2012, 1 Page.

* cited by examiner

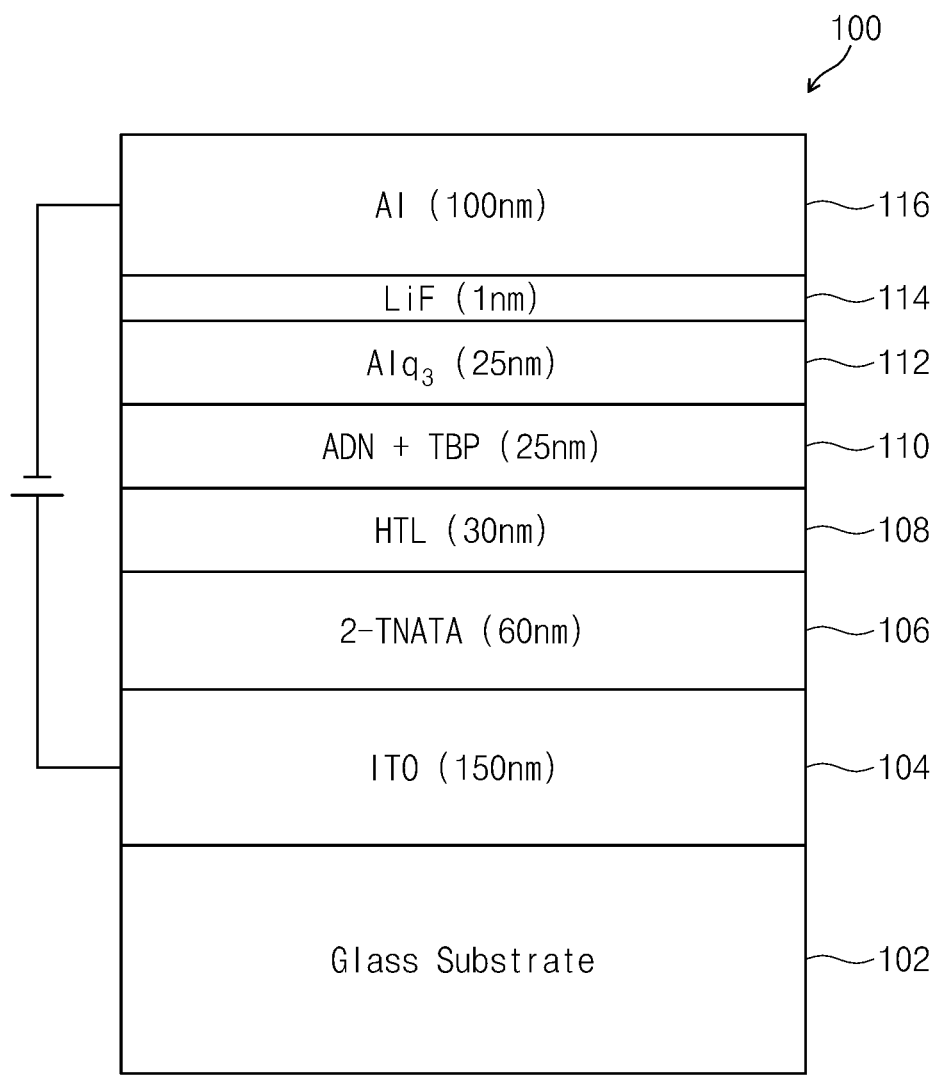

ORGANIC ELECTROLUMINESCENT MATERIAL AND ORGANIC ELECTROLUMINESCENT DEVICE INCLUDING THE SAME

CROSS-REFERENCE TO RELATED APPLICATION

This U.S. non-provisional patent application claims priority to and the benefit of Japanese Patent Application No. 2014-214447, filed on Oct. 21, 2014, the entire content of which is hereby incorporated by reference.

BACKGROUND

1. Field

One or more aspects of embodiments of the present disclosure relate to a material for an organic electroluminescent device and an organic electroluminescent device including the material. The organic electroluminescent device including the material of embodiments of the present disclosure can be driven at a low voltage in a blue emission region and can exhibit high emission efficiency.

2. Description of the Related Art

Recently, an organic electroluminescent display (hereinafter, "organic EL display") has been actively developed as an image display apparatus. The organic EL display, unlike a liquid crystal display or the like, is a self luminescent type (or kind) of display which is capable of displaying images via light emission of a luminescent material including an organic compound. For example, holes and electrons injected from an anode and a cathode can be recombined in an emission layer including the luminescent material to emit light.

For example, an organic electroluminescent device (organic EL device) may include an anode, a hole transport layer positioned on the anode, an emission layer on the hole transport layer, an electron transport layer on the emission layer, and a cathode on the electron transport layer. Holes are injected from the anode, and are transported via the hole transport layer into the emission layer. Electrons are injected from the cathode, and are transported via the electron transport layer into the emission layer. The holes and the electrons injected into the emission layer are then recombined, and excitons are generated in the emission layer. The organic EL device emits light using light generated by the radiation deactivation of the excitons. The organic EL device is not limited to the aforementioned configuration, and may include modifications thereof.

The organic EL device included in a display device is required to be driven at a low voltage and have high efficiency and long life. For example, in a blue emission region, the driving voltage of an organic EL device may be too high and the emission efficiency thereof may be insufficient when compared to those in a green emission region and/or a red emission region. To realize a low driving voltage, high efficiency, and long life of the organic EL device, the normalization, the stabilization, and/or the like of the hole transport layer may be examined. For example, an aromatic amine compound can be utilized as a material for the organic EL device, however the carrier tolerance of such material is relatively low, and thus the life of the organic EL device may remain low.

To increase the life of the organic EL device, an amine derivative substituted with, for example, a heteroaryl ring has been proposed. However, the organic EL device using the above-described material has not been shown to sufficiently realize low driving voltage, high emission efficiency, and long life, and thus there is still a need for an organic EL device having low driving voltage, high emission efficiency, and long life. Particularly, since the emission efficiency of the organic EL device in a blue emission region is relatively low when compared to that in a red emission region and/or a green emission region, increased emission efficiency in the blue emission region is required. Accordingly, there is a need for the development of a novel material capable of realizing an organic EL device having low driving voltage, high emission efficiency, and long life.

SUMMARY

One or more aspects of embodiments of the present disclosure are directed toward a material capable of realizing an organic EL device that may be driven at a low voltage and may have high emission efficiency and long life.

One or more embodiments of the present disclosure are directed toward a material capable of realizing an organic EL device that may be driven at a low voltage and may have high emission efficiency and long life in a blue emission region, the material being included in at least one layer selected from the stacked layers positioned between the emission layer and the anode of the organic EL device.

In one or more embodiments of the present disclosure, a material for an organic EL device is represented by the following General Formula (1):

General Formula (1)

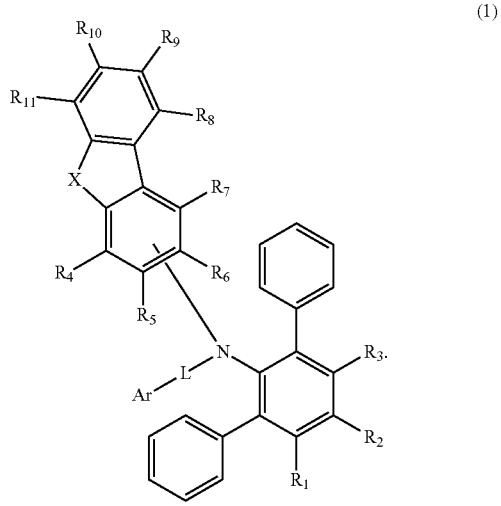

In the above General Formula (1), X may be selected from an oxygen atom, a sulfur atom, $CR_{12}R_{13}$, $SiR_{14}R_{15}$ and $NR_{16}$; $R_1$ to $R_{16}$ may be each independently selected from a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a silyl group, a halogen atom, a hydrogen atom and a deuterium atom; L may be selected from a direct linkage, a substituted or unsubstituted arylene group having 6 to 30 carbon atoms for forming a ring, a substituted or unsubstituted heteroarylene group having 1 to 30 carbon atoms for forming a ring and a divalent silyl group; and Ar may be selected from a substituted or unsubstituted aryl group having 6 to 30 carbon atoms for forming a ring and a substituted or unsubstituted heteroaryl group having 1 to 30 carbon atoms for forming a ring.

The material for an organic EL device according to embodiments of the present disclosure includes a dibenzoheterole part or a fluorene part coupled with [1,1':3',1''-terphenyl]-2'-amino group, and thus amine properties may be maintained and amorphous properties may be improved. When the above-described material is utilized as the material for the manufacture of the organic EL device, low driving voltage, high emission efficiency and long life of the organic EL device may be realized. For example, improved properties of the organic EL device may be obtained in a blue emission region.

In some embodiments, $R_2$ in General Formula (1) may be a phenyl group, and the material represented by General Formula (1) may be represented by the following General Formula (2):

General Formula (2)

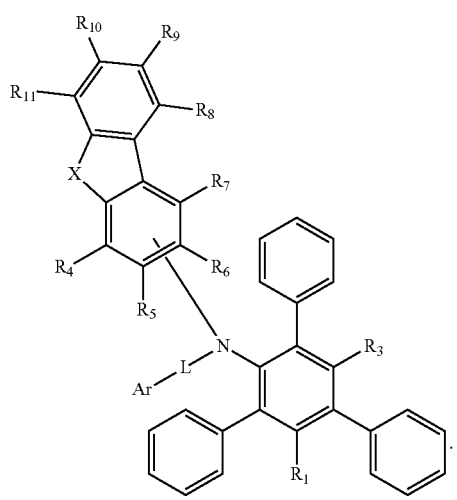

(2)

The material for an organic EL device according to embodiments of the present disclosure includes a dibenzoheterole part or a fluorene part coupled with a large volume 5'-phenyl-[1,1':3',1''-terphenyl]-2'-amino group, and thus amine properties may be maintained and amorphous properties may be improved. When the above-described material is utilized as the material for the manufacture of the organic EL device, low driving voltage, high emission efficiency and long life of the organic EL device may be realized. For example, improved properties of the organic EL device may be obtained in a blue emission region.

In some embodiments, in General Formula (1), $R_1$ and $R_3$ may each independently be a hydrogen atom or a deuterium atom, $R_2$ may be a phenyl group, and $R_5$ may form a direct linkage with N, and the material represented by General Formula (1) may be represented by the following General Formula (3):

General Formula (3)

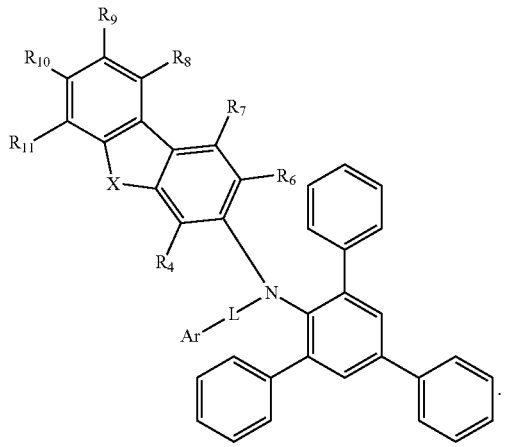

(3)

The material for an organic EL device according to embodiments of the present disclosure includes a dibenzoheterole part or a fluorene part coupled with a large volume 5'-phenyl-[1,1':3',1''-terphenyl]-2'-amino group, and thus amine properties may be maintained and amorphous properties may be improved. When the above-described material is utilized as the material for the manufacture of the organic EL device, low driving voltage, high emission efficiency and long life of the organic EL device may be realized. For example, improved properties of the organic EL device may be obtained in a blue emission region.

In some embodiments, adjacent groups selected from $R_1$ to $R_{16}$ may combine with each other (e.g., may be coupled to each other) to form a saturated or unsaturated ring.

In some embodiments of the present disclosure, an organic EL device includes the material for an organic EL device in at least one layer selected from the stacked layers positioned between the emission layer and the anode.

The material for an organic EL device according to embodiments of the present disclosure includes a dibenzoheterole part or a fluorene part coupled with [1,1':3',1''-terphenyl]-2'-amino group, and thus amine properties may be maintained and amorphous properties may be improved. When the above-described material is utilized as the material for the manufacture of the organic EL device, low driving voltage, high emission efficiency and long life of the organic EL device may be realized. For example, improved properties of the organic EL device may be obtained in a blue emission region.

BRIEF DESCRIPTION OF THE DRAWING

The accompanying drawing is included to provide a further understanding of the present disclosure, and is incorporated in and constitutes a part of this specification. The drawing illustrates example embodiments of the present disclosure and, together with the description, serves to explain principles of the present disclosure. The drawing is a schematic view illustrating an organic EL device according to one or more embodiments of the present disclosure.

DETAILED DESCRIPTION

According to one or more embodiments of the present disclosure, an organic EL device (including the material having a dibenzoheterole part or a fluorene part coupled with [1.1'-:3',1''-terphenyl]-2'-amino group) may have low driving voltage, high emission efficiency and long life, while also maintaining amine properties and improving amorphous properties.

Hereinafter, the material for an organic EL device and the organic EL device including the same according to embodiments of the present disclosure will be described with reference to the accompanying drawing. The material for an organic EL device and the organic EL device using the same according to embodiments of the present disclosure may, however, be embodied in different forms and should not be construed as limited to the embodiments set forth herein. In the drawing, like reference numerals refer to like elements or elements having like functions throughout, and repeated explanations of these elements will not be provided.

The material for an organic EL device according to one or more embodiments of the present disclosure includes a material represented by General Formula (1):

General Formula (1)

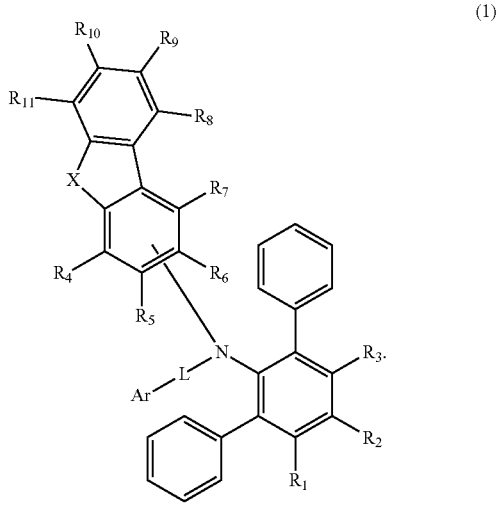

(1)

In General Formula (1), X may be selected from an oxygen atom (e.g., —O—), a sulfur atom (e.g., —S—), $CR_{12}R_{13}$, $SiR_{14}R_{15}$ and $NR_{16}$. $R_1$ to $R_{16}$ may be each independently selected from a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a silyl group, a halogen atom, a hydrogen atom and a deuterium atom. L may be selected from a direct linkage, a substituted or unsubstituted arylene group having 6 to 30 carbon atoms for forming a ring, a substituted or unsubstituted heteroarylene group having 1 to 30 carbon atoms for forming a ring and a divalent silyl group. Ar may be selected from a substituted or unsubstituted aryl group having 6 to 30 carbon atoms for forming a ring and a substituted or unsubstituted heteroaryl group having 1 to 30 carbon atoms for forming a ring. As used herein, the statement "atoms for forming a ring" may refer to "ring-forming atoms." As used herein, the statement "direct linkage" may refer to "a chemical bond, such as a single bond."

Here, the substituted or unsubstituted aryl group having 6 to 30 carbon atoms for forming a ring used in, for example, any of $R_1$ to $R_{16}$ may include a phenyl group, a naphthyl group, an anthracenyl group, a phenanthryl group, a biphenyl group, a terphenyl group, a quaterphenyl group, a quinqphenyl group, a sexiphenyl group, a fluorenyl group, a triphenylenyl group, a biphenylenyl group, a pyrenyl group, a benzofluoranthenyl group, a glyceryl group, and/or the like, but is not limited thereto.

The substituted or unsubstituted heteroaryl group having 1 to 30 carbon atoms for forming a ring used in, for example, any of $R_1$ to $R_{16}$ may include a benzothiazolyl group, a thiophenyl group, a thienothiophenyl group, a thienothienothiophenyl group, a benzothiophenyl group, a benzofuryl group, a dibenzothiophenyl group, an N-arylcarbazolyl group, an N-heteroarylcarbazolyl group, an N-alkylcarbazolyl group, a phenoxazyl group, a phenothiazyl group, a pyridyl group, a pyrimidyl group, a triazile group, a quinolinyl group, a quinoxalyl group, and/or the like, but is not limited thereto.

The alkyl group having 1 to 15 carbon atoms used in, for example, any of $R_1$ to $R_{16}$ may include a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, and/or the like, but is not limited thereto.

In some embodiments, the substituted or unsubstituted arylene group having 6 to 30 carbon atoms for forming a ring used in, for example, L may include a divalent version of a phenyl group, a naphthyl group, an anthracenyl group, a phenanthryl group, a biphenyl group, a terphenyl group, a quaterphenyl group, a quinqphenyl group, a sexiphenyl group, a fluorenyl group, a triphenylenyl group, a biphenylenyl group, a pyrenyl group, a benzofluoranthenyl group, a glyceryl group, and/or the like, but is not limited thereto.

In some embodiments, the substituted or unsubstituted heteroarylene group having 1 to 30 carbon atoms for forming a ring used in, for example, L may include a divalent version of a benzothiazolyl group, a thiophenyl group, a thienothiophenyl group, a thienothienothiophenyl group, a benzothiophenyl group, a benzofuryl group, a dibenzothiophenyl group, an N-arylcarbazolyl group, an N-heteroarylcarbazolyl group, an N-alkylcarbazolyl group, a phenoxazyl group, a phenothiazyl group, a pyridyl group, a pyrimidyl group, a triazile group, a quinolinyl group, a quinoxalyl group, and/or the like, but is not limited thereto.

The substituted or unsubstituted aryl group having 6 to 30 carbon atoms for forming a ring used in, for example, Ar may include a phenyl group, a naphthyl group, an anthracenyl group, a phenanthryl group, a biphenyl group, a terphenyl group, a quaterphenyl group, a quinqphenyl group, a sexiphenyl group, a fluorenyl group, a triphenylenyl group, a biphenylenyl group, a pyrenyl group, a benzofluoranthenyl group, a glyceryl group, and/or the like, but is not limited thereto.

The substituted or unsubstituted heteroaryl group having 1 to 30 carbon atoms for forming a ring used in, for example, Ar may include a benzothiazolyl group, a thiophenyl group, a thienothiophenyl group, a thienothienothiophenyl group, a benzothiophenyl group, a benzofuryl group, a dibenzothiophenyl group, an N-arylcarbazolyl group, an N-heteroarylcarbazolyl group, an N-alkylcarbazolyl group, a phenoxazyl group, a phenothiazyl group, a pyridyl group, a pyrimidyl group, a triazile group, a quinolinyl group, a quinoxalyl group, and/or the like, but is not limited thereto.

The material for an organic EL device according to embodiments of the present disclosure includes a dibenzoheterole part or a fluorene part coupled with [1,1':3',1''-terphenyl]-2'-amino group, and thus amine properties may be maintained and amorphous properties may be improved. When the above-described material is utilized as the material for the manufacture of the organic EL device, low driving voltage, high emission efficiency and long life of the organic EL device may be realized. For example, improved properties of the organic EL device may be obtained in a blue emission region.

In some embodiments, $R_2$ in General Formula (1) may be a phenyl group, and the material of General Formula (1) may be represented by the following General Formula (2):

General Formula (2)

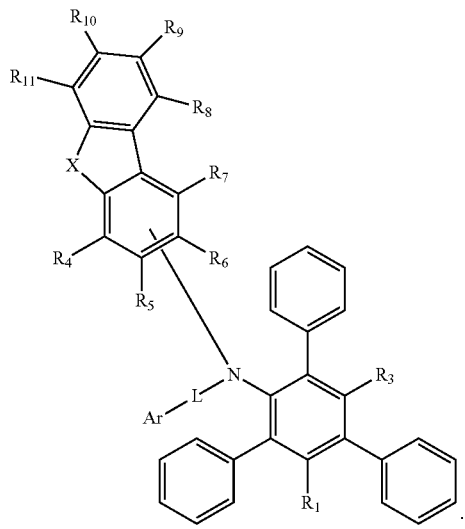

(2)

The material for an organic EL device according to embodiments of the present disclosure includes a dibenzoheterole part or a fluorene part coupled with a large volume 5'-phenyl-[1,1':3',1''-terphenyl]-2'-amino group, and thus amine properties may be maintained and amorphous properties may be improved. When the above-described material is utilized as the material for the manufacture of the organic EL device, low driving voltage, high emission efficiency and long life of the organic EL device may be realized. For example, improved properties of the organic EL device may be obtained in a blue emission region.

In some embodiments, in the material for an organic EL device of General Formula (1), $R_1$ and $R_3$ may be each independently a hydrogen atom or a deuterium atom, $R_2$ may be a phenyl group, and $R_5$ may form a direct linkage with N, and the material of General Formula (1) for an organic EL device according to embodiments of the present disclosure may be represented by the following General Formula (3):

General Formula (3)

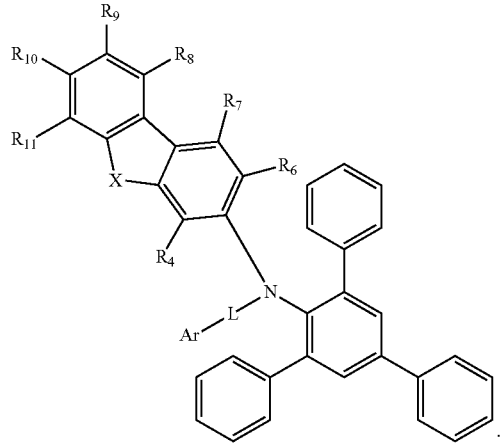

(3)

In some embodiments, when X in General Formula (1) is the oxygen atom or the sulfur atom, $R_5$ in General Formula (1) may be combined at (e.g., may be coupled at) position 3, as illustrated by the following General Formula (4). However, embodiments of the present disclosure are not limited thereto.

General Formula (4)

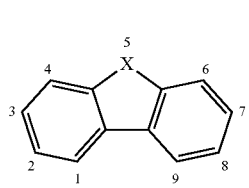

(4)

In some embodiments, when X in General Formula (1) is $CR_{12}R_{13}$, $SiR_{14}R_{15}$ or $NR_{16}$, $R_5$ in General Formula (1) may be combined at (e.g., may be coupled at) position 2, as illustrated by the following General Formula (5). However, embodiments of the present disclosure are not limited thereto. In General Formula (5), H may represent one or more substituents of X.

General Formula (5)

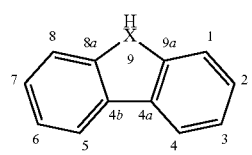

The numbering of the substitution positions in the dibenzoheterole ring represented by General Formula (4) is assigned by positioning the dibenzoheterole ring so that the hetero atom is at the bottom site thereof (e.g., facing the bottom of the page), assigning the first position to the right-hand uppermost skeleton atom of the ring (here, carbon atom at a condensed position adjacent to X is excluded), and then consecutively numbering the remaining positions clockwise, while excluding carbon atoms at condensed positions. The numbering of the substitution positions in the dibenzoheterole ring represented by General Formula (5) (e.g., in the carbazole ring represented by General Formula (5)), is assigned by positioning the dibenzoheterole ring so that X (including e.g., a carbon atom, a silicon atom or a nitrogen atom) is positioned at the top site thereof (e.g., facing the top of the page), assigning the first position to the right-hand and uppermost skeleton atom of the ring (here, carbon atom at a condensed position 9a adjacent to X is excluded), and then consecutively numbering the remaining positions clockwise, while excluding carbon atoms at condensed positions 4a, 4b, and 8a.

The material for an organic EL device according to embodiments of the present disclosure includes a dibenzoheterole part or a fluorene part coupled with a large volume 5'-phenyl-[1,1':3',1"-terphenyl]-2'-amino group, and thus amine properties may be maintained and amorphous properties may be improved. When the above-described material is utilized as the material for the manufacture of the organic EL device, low driving voltage, high emission efficiency and long life of the organic EL device may be realized. For example, improved properties of the organic EL device may be obtained in a blue emission region.

In the material for an organic EL device according to embodiments of the present disclosure, adjacent groups selected from $R_1$ to $R_{16}$ may combine with each other (e.g., may be coupled to each other) to form a saturated or unsaturated ring.

The material for an organic EL device according to embodiments of the present disclosure may include at least one compound selected from Compounds 1 to 8 illustrated below:

1

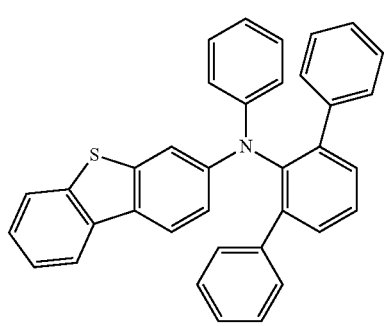

2

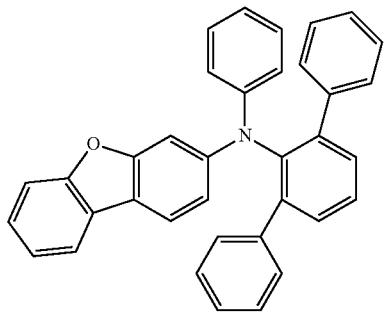

3

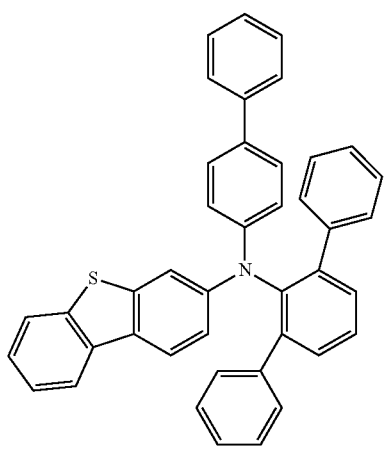

4

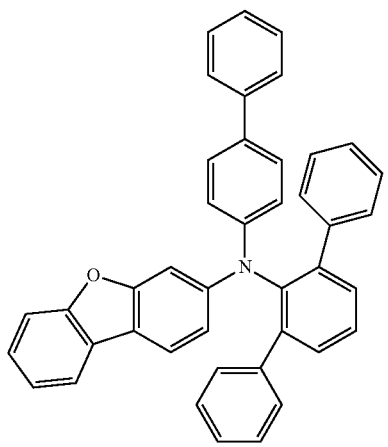

5

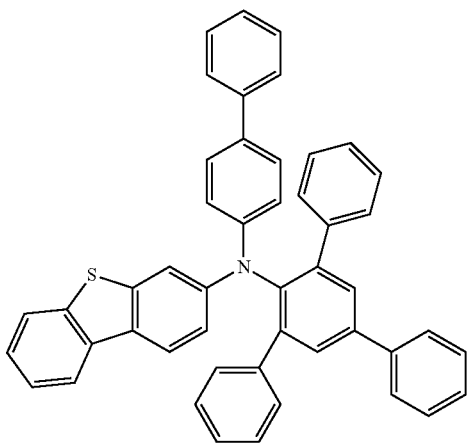

-continued
6
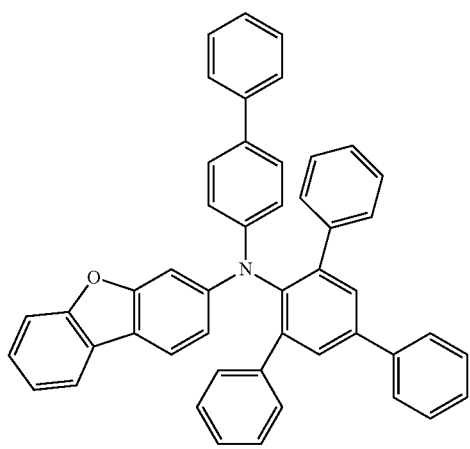
7
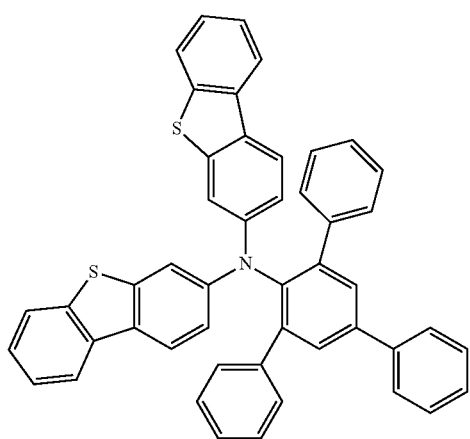
8
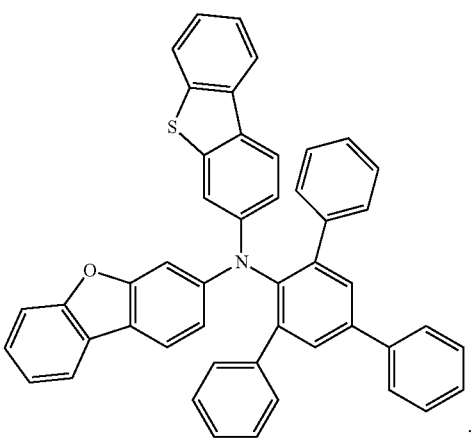
9
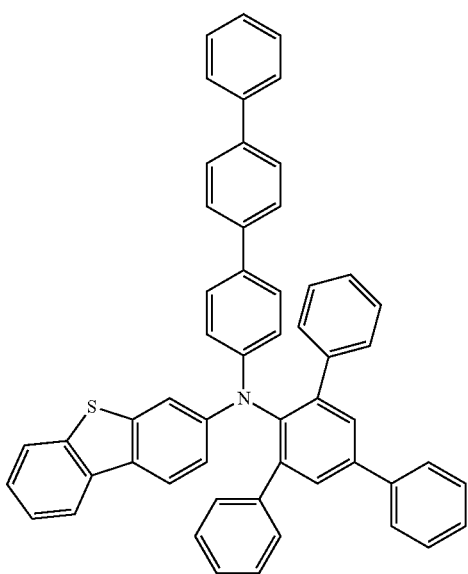
10
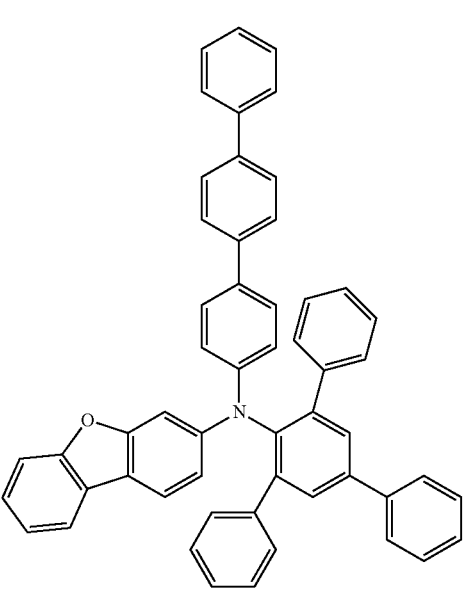
11
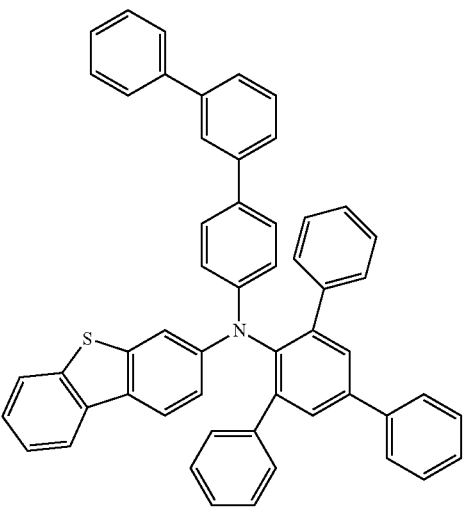
In some embodiments, the material for an organic EL device according to embodiments of the present disclosure may include at least one compound selected from Compounds 9 to 15 illustrated below:

12
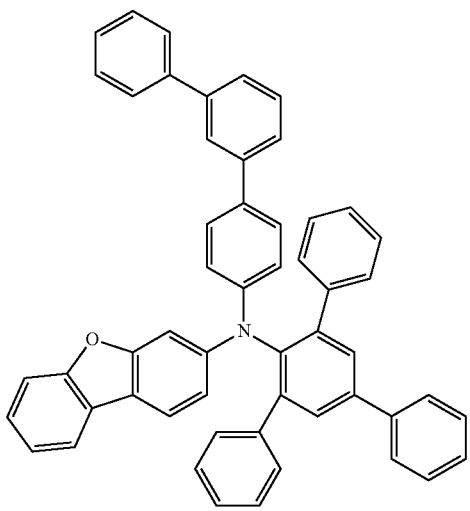
13
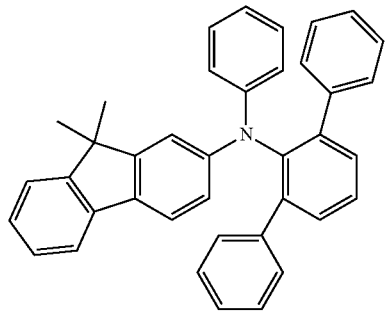
14
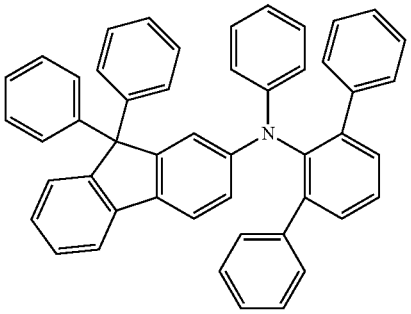
15
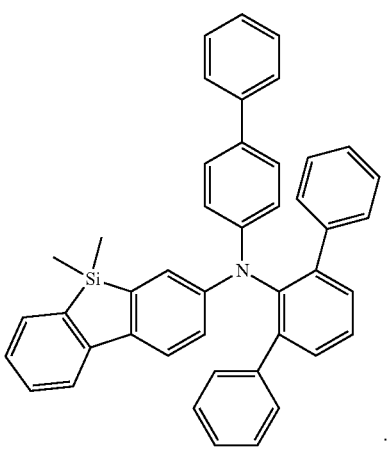
In some embodiments, the material for an organic EL device according to embodiments of the present disclosure may include at least one compound selected from Compounds 16 to 21 illustrated below:
16
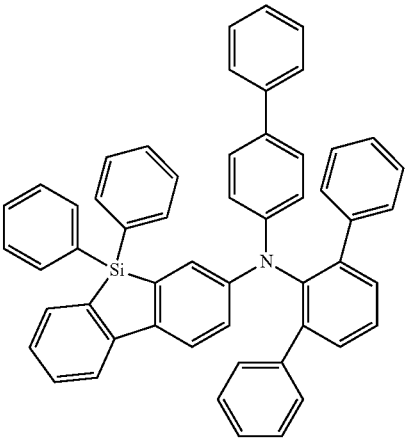
17
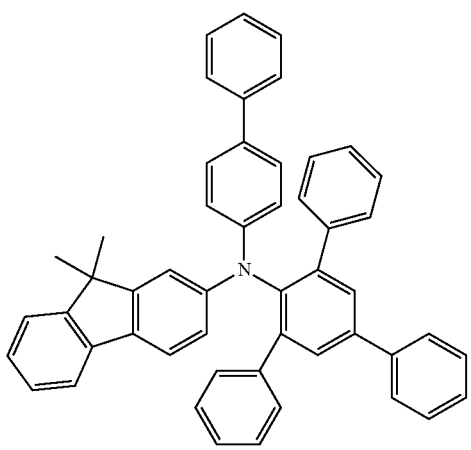
18
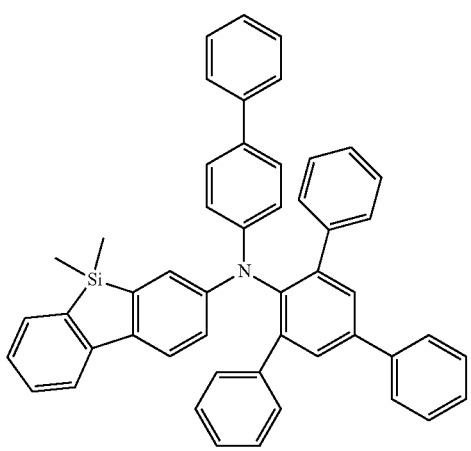

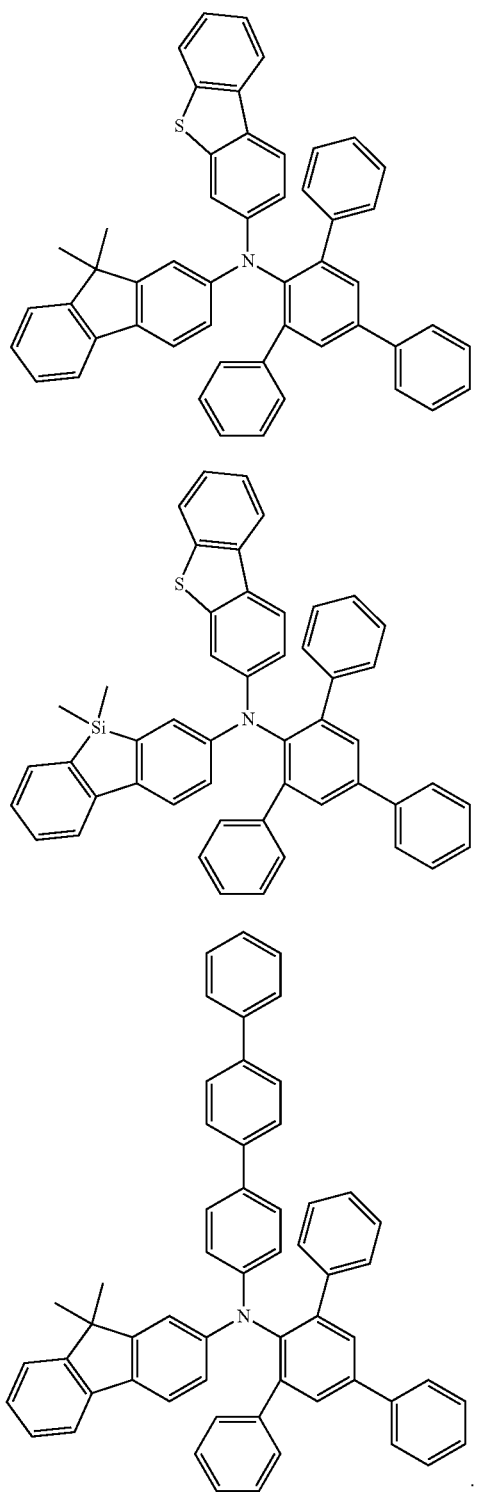
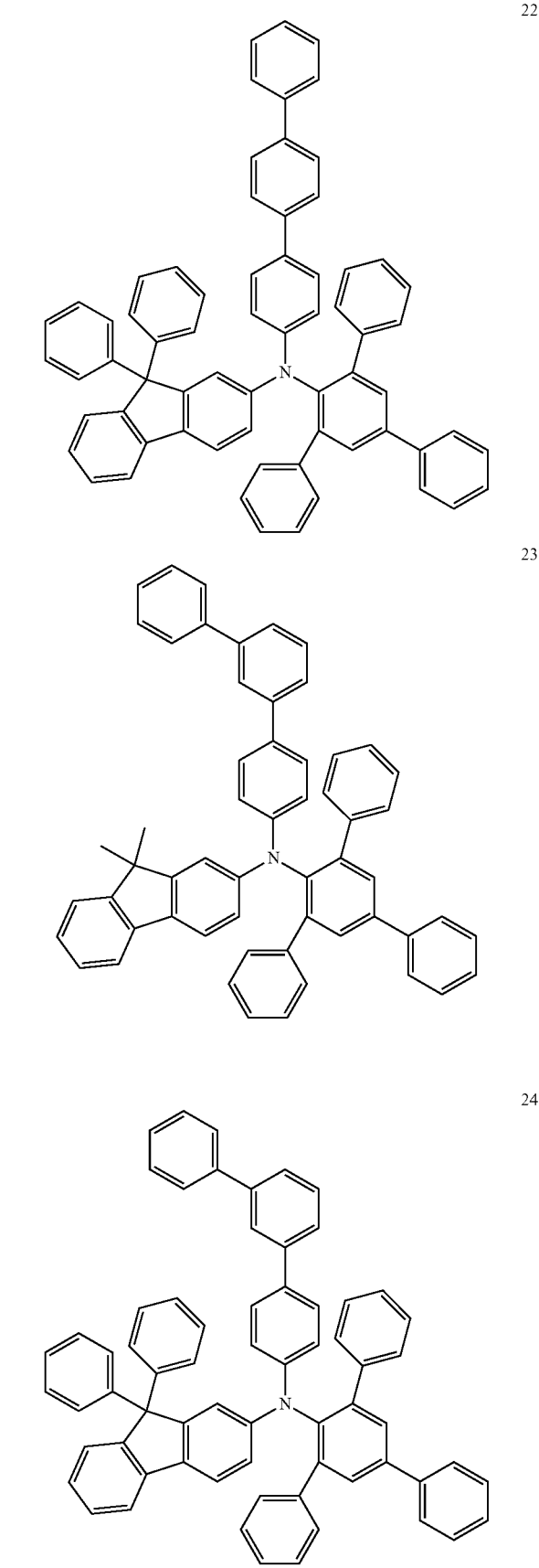
In some embodiments, the material for an organic EL device according to embodiments of the present disclosure may include at least one compound selected from Compounds 22 to 27 illustrated below:

25
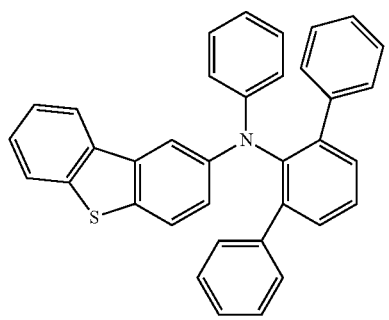
26
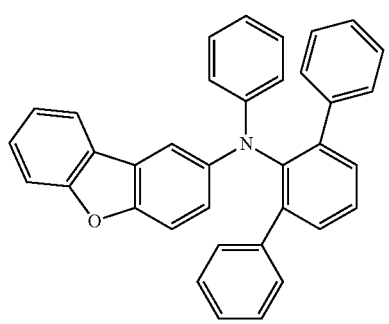
27
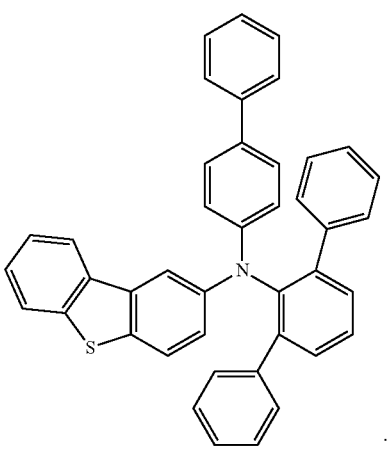
28
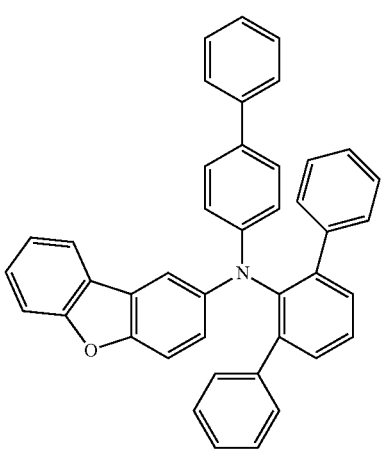
29
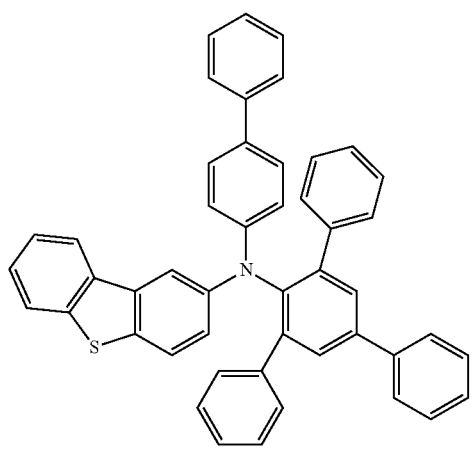
30
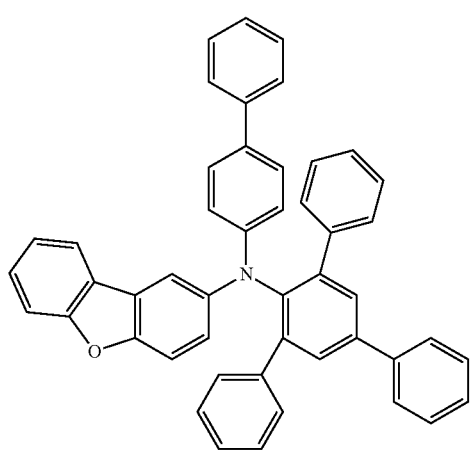
In some embodiments, the material for an organic EL device according to embodiments of the present disclosure may include at least one compound selected from Compounds 28 to 34 illustrated below:

31
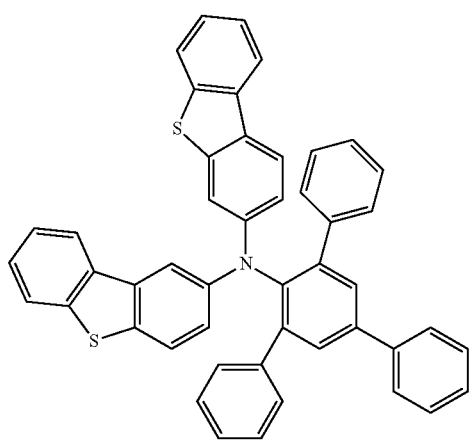
32
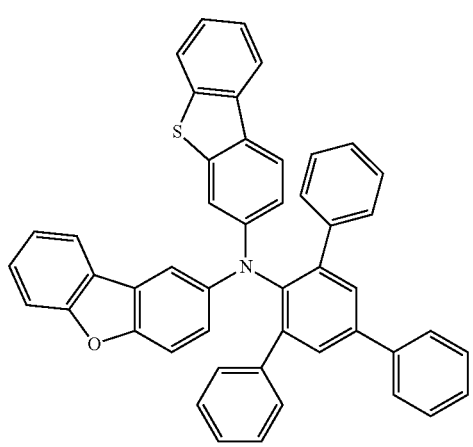
33
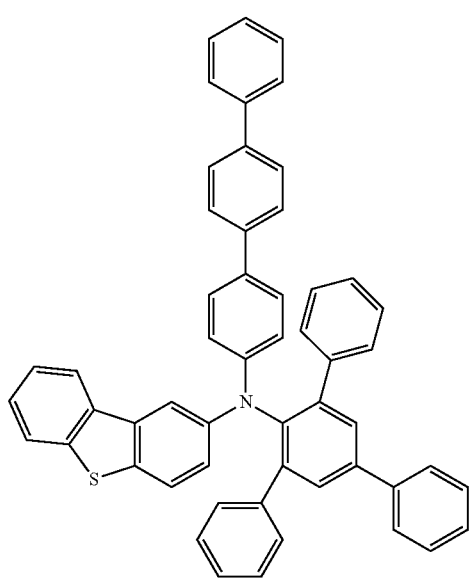
34
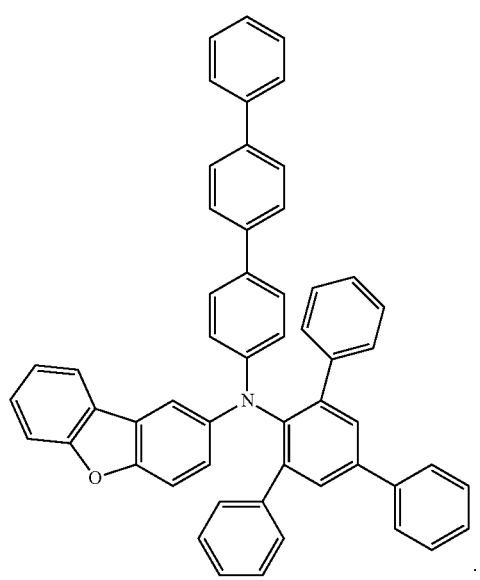
In some embodiments, the material for an organic EL device according to embodiments of the present disclosure may include at least one compound selected from Compounds 35 to 42 illustrated below:
35
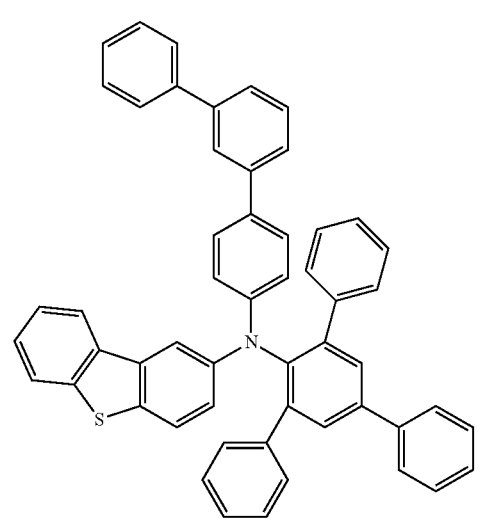

36
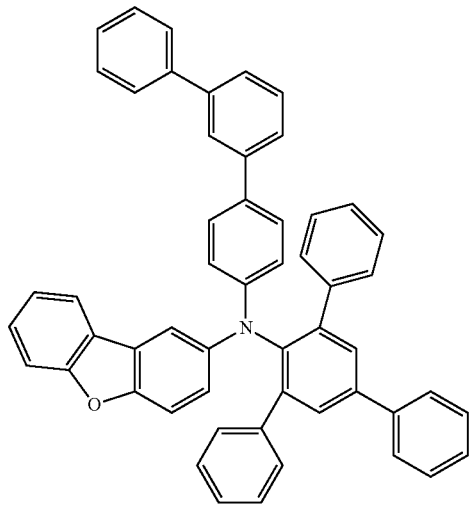
37
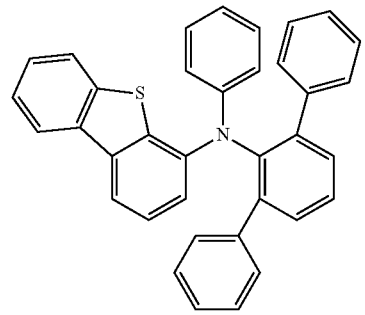
38
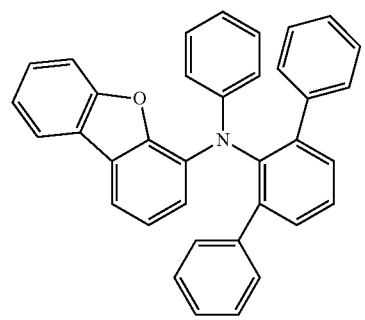
39
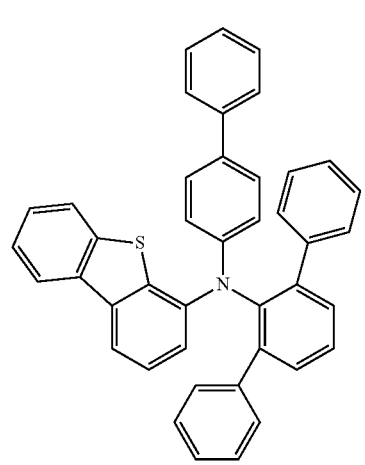
40
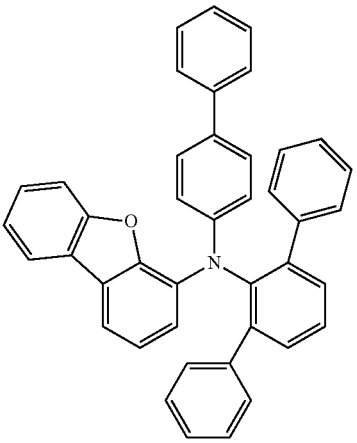
41
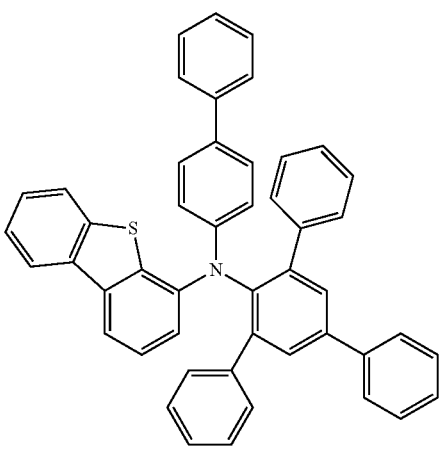
42
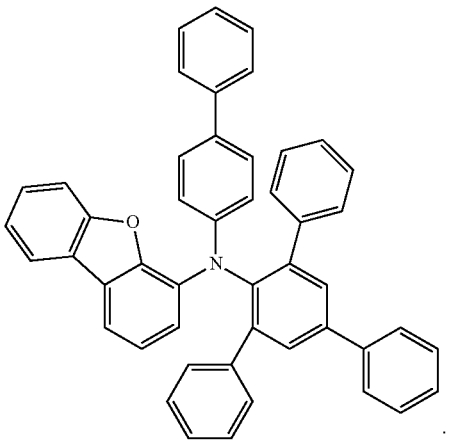
In some embodiments, the material for an organic EL device according to embodiments of the present disclosure may include at least one compound selected from Compounds 43 to 50 illustrated below:

43
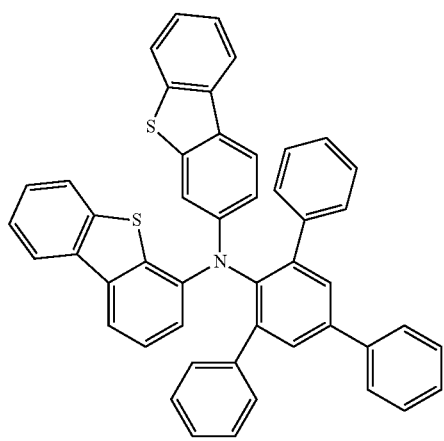
44
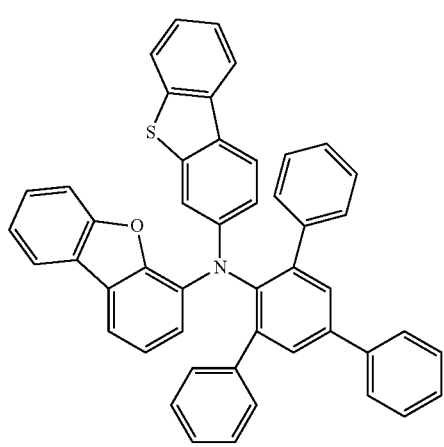
45
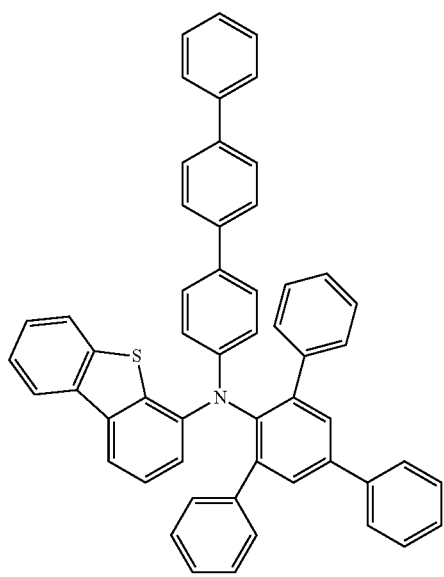
46
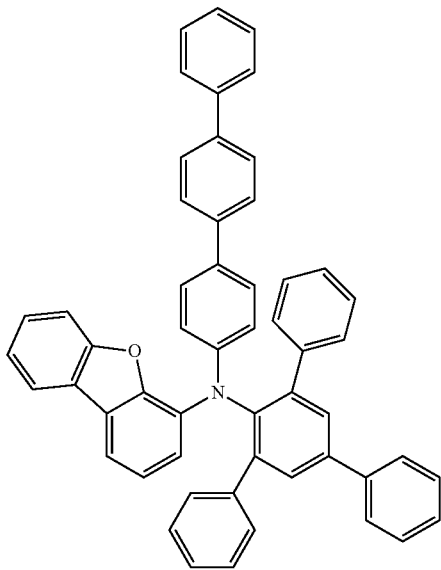
47
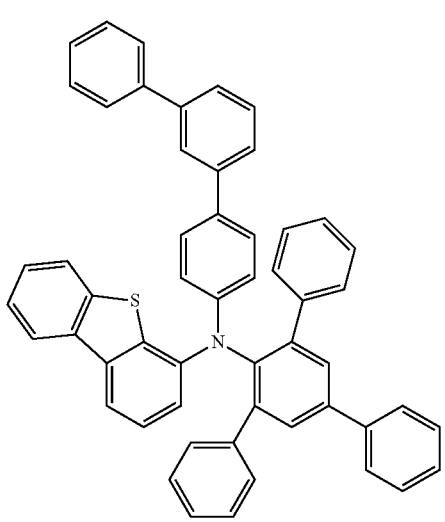
48
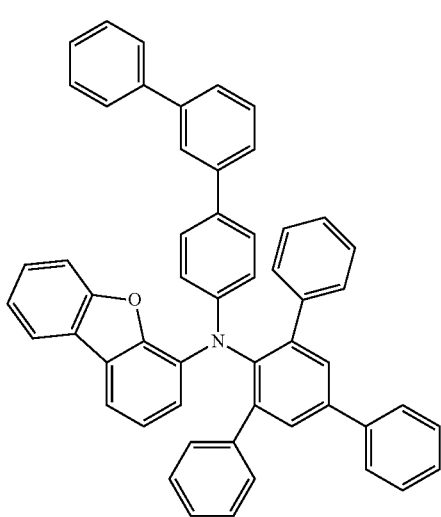

49
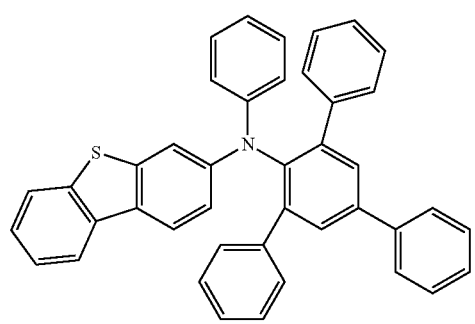
50
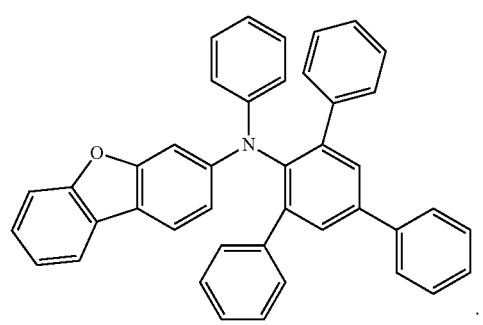
In some embodiments, the material for an organic EL device according to embodiments of the present disclosure may include at least one compound selected from Compounds 51 to 57 illustrated below:
51
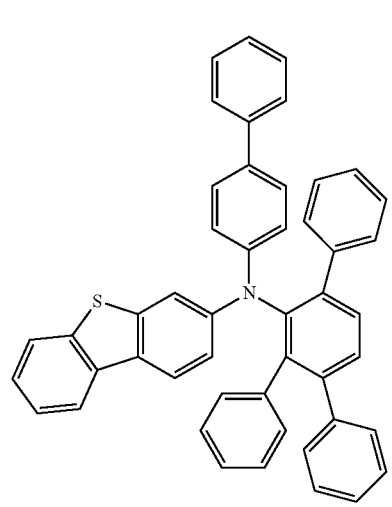
52
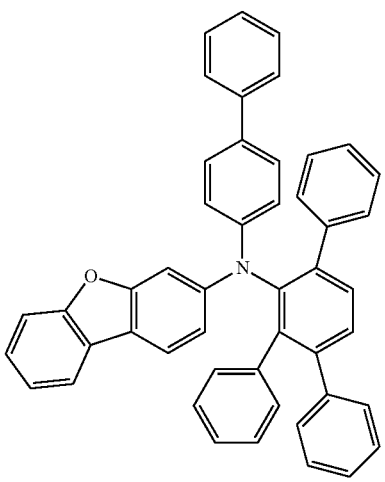
53
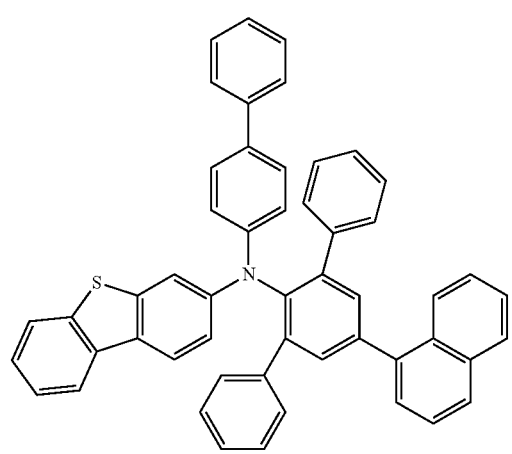
54
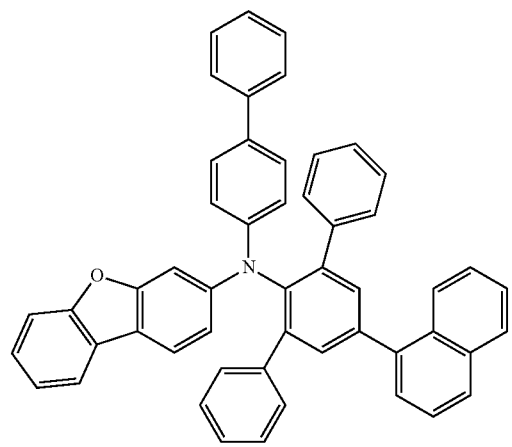

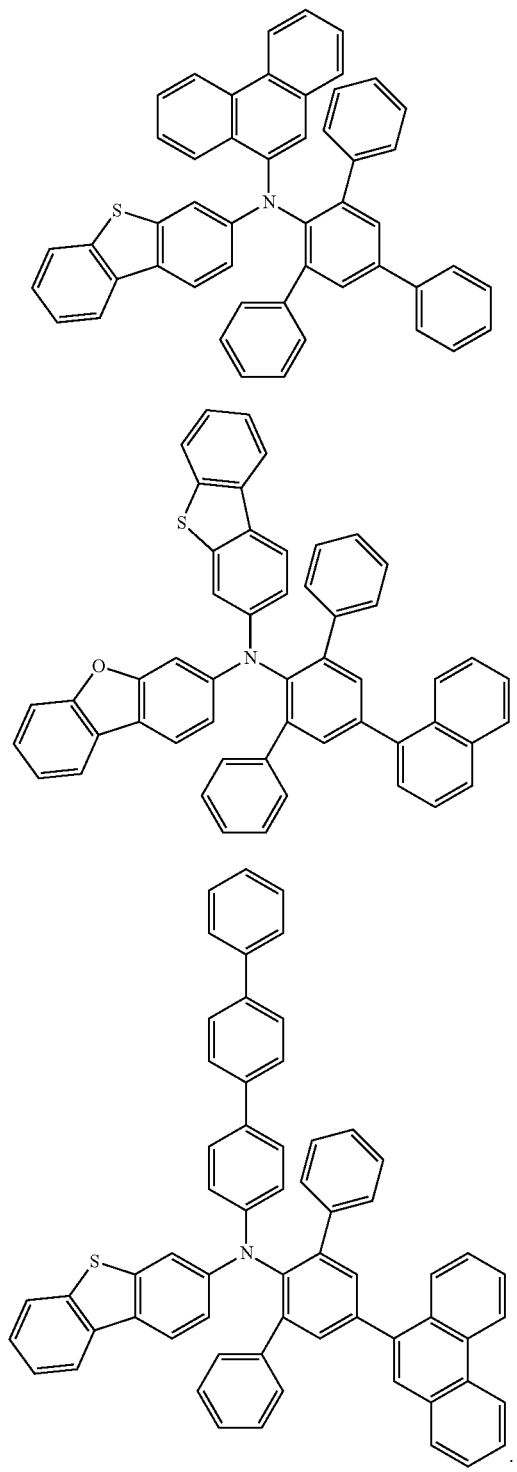
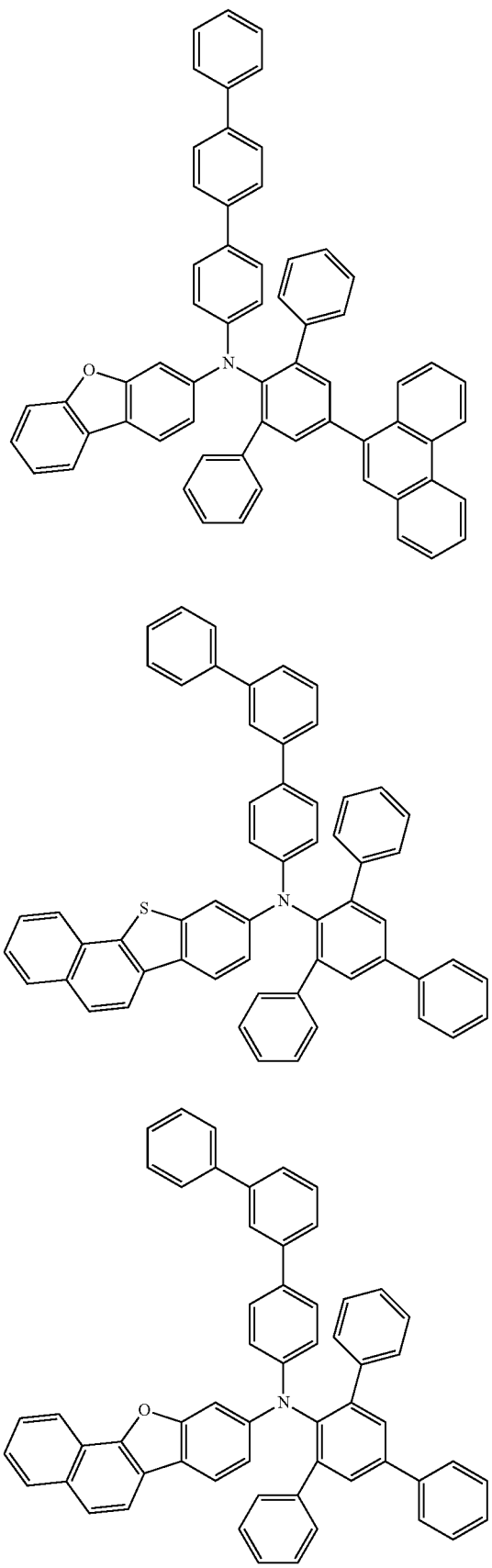
In some embodiments, the material for an organic EL device according to embodiments of the present disclosure may include at least one compound selected from Compounds 58 to 64 illustrated below:

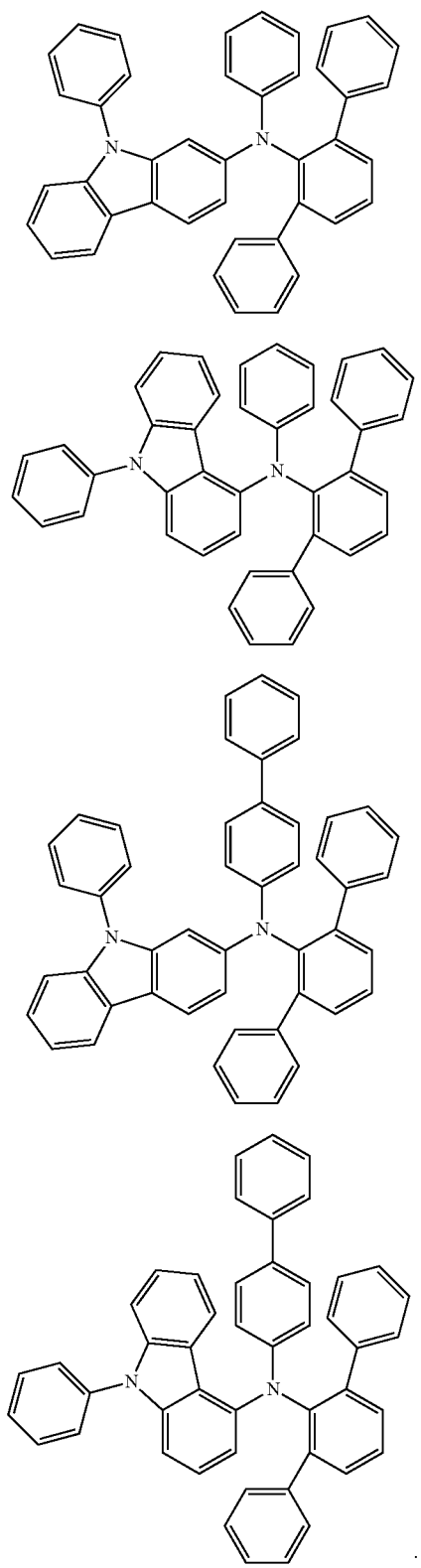
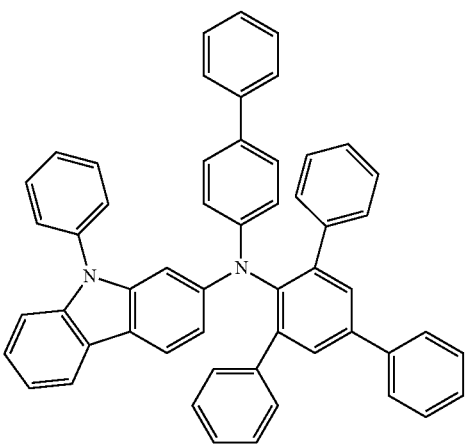
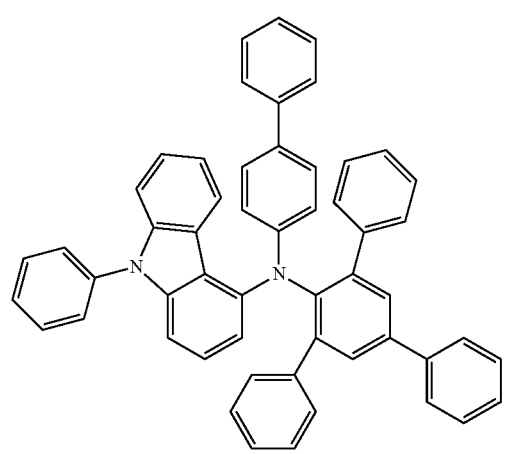
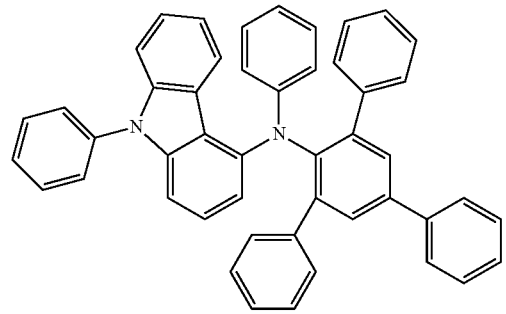
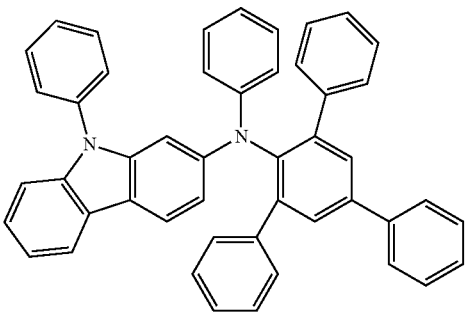
In some embodiments, the material for an organic EL device according to embodiments of the present disclosure may include at least one compound selected from Compounds 65 to 70 illustrated below:

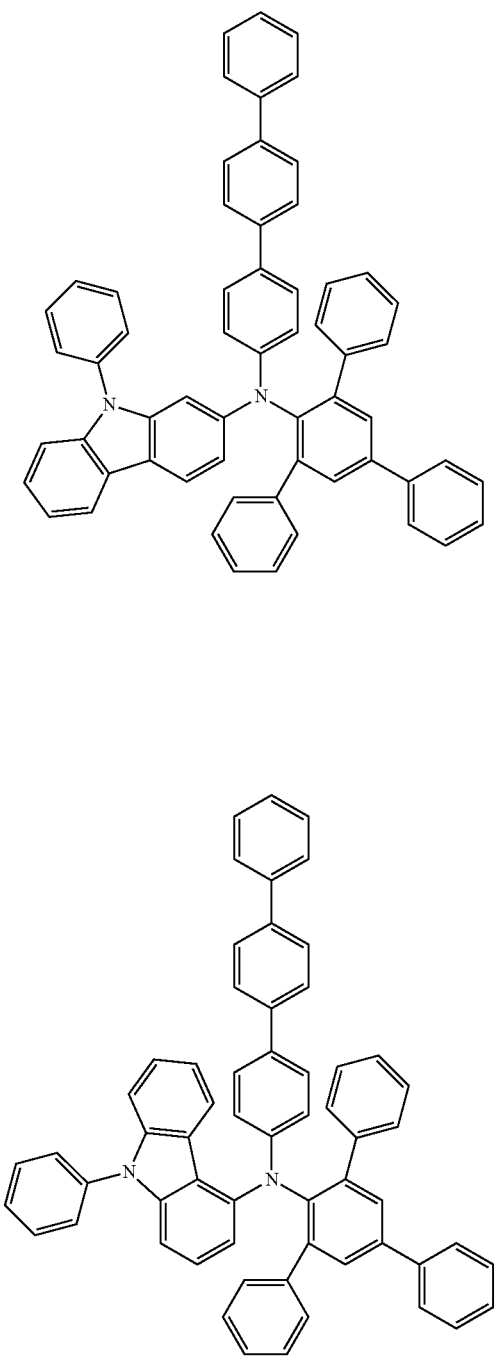
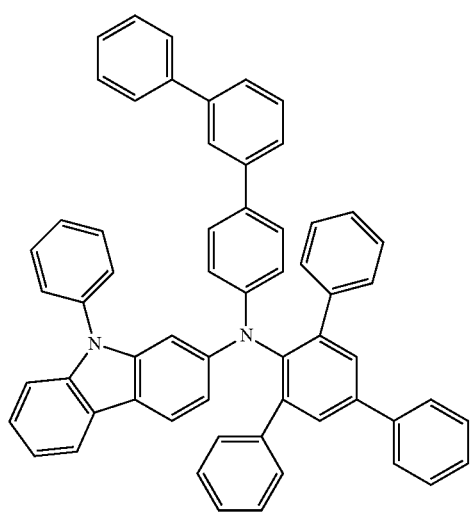
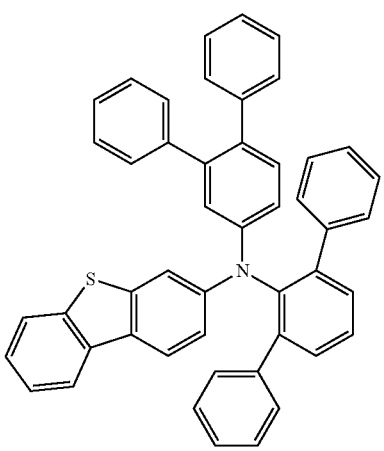
In some embodiments, the material for an organic EL device according to embodiments of the present disclosure may include at least one compound selected from Compounds 71 to 78 illustrated below:

74
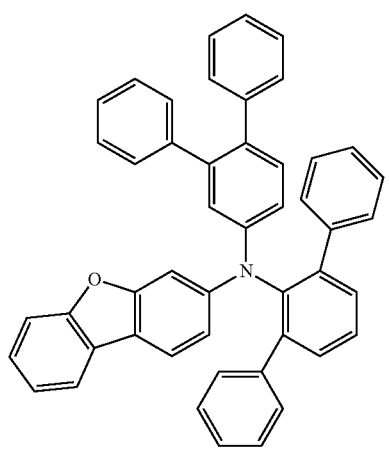
75
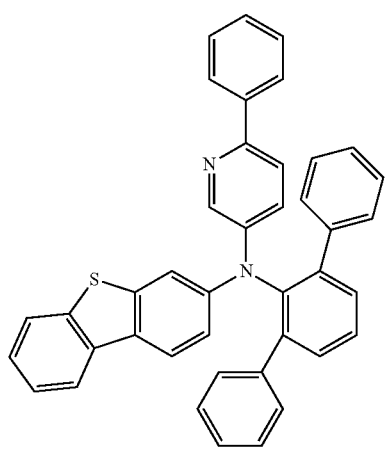
76
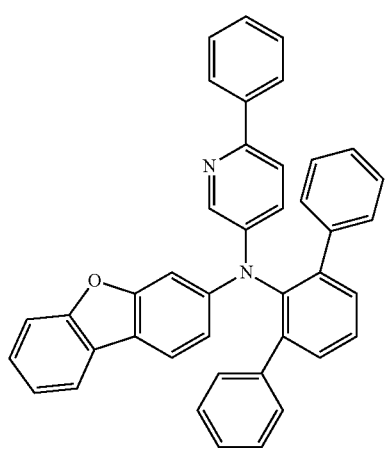
77
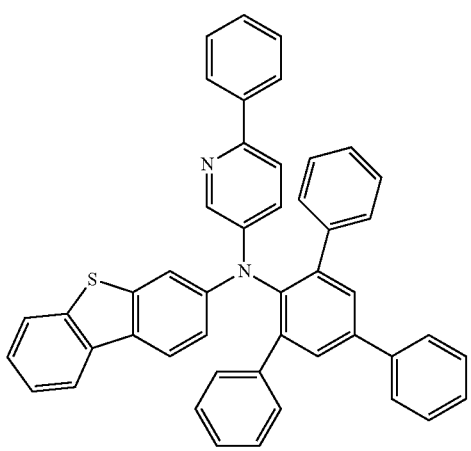
78
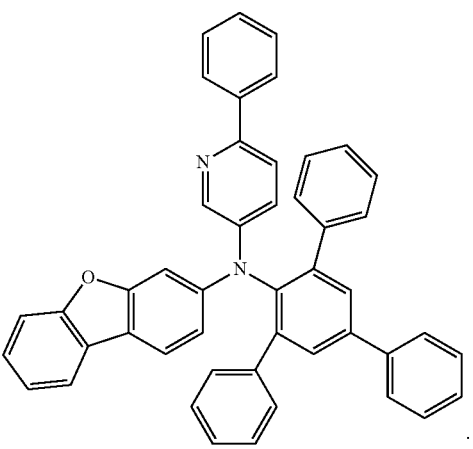
In some embodiments, the material for an organic EL device according to embodiments of the present disclosure may include at least one compound selected from Compounds 79 to 84 illustrated below:
79
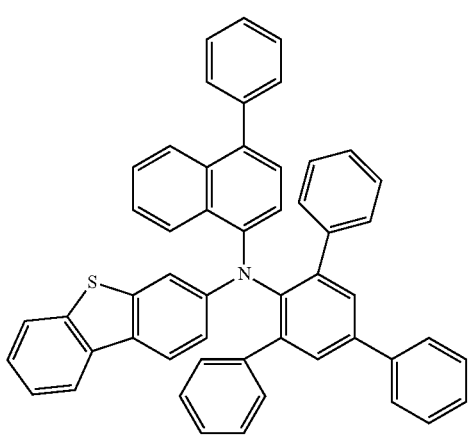

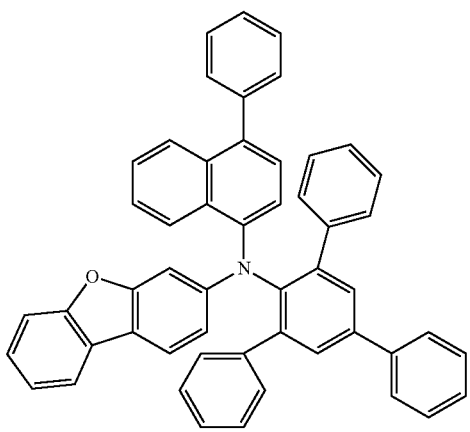

80

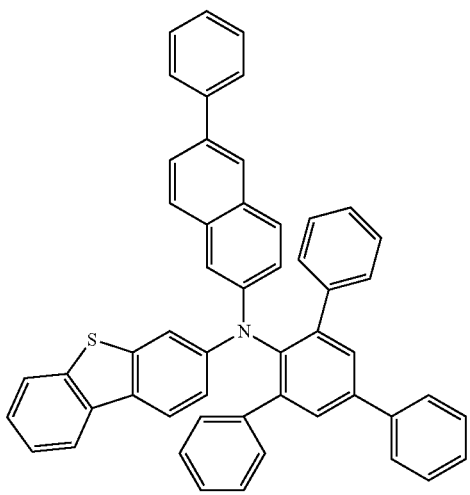

81

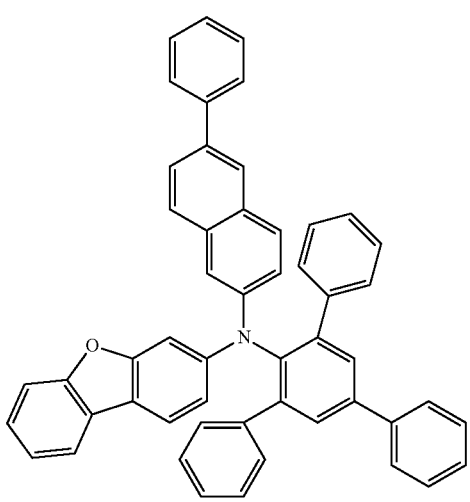

82

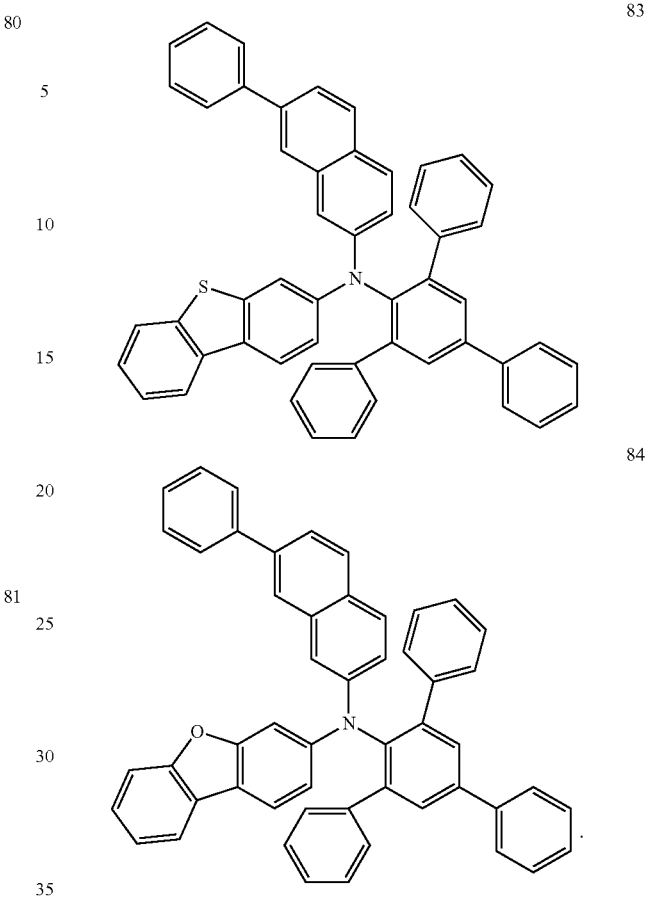

The material for an organic EL device according to embodiments of the present disclosure may be used in at least one layer selected from the stacked layers positioned between the emission layer and the anode of an organic EL device. Accordingly, the amine properties may be maintained, and the amorphous properties of the material may be improved, and so, low driving voltage, high emission efficiency and long life of the organic EL device may be realized.

(Organic EL Device)

Hereinafter, an organic EL device according to one or more embodiments of the present disclosure will be described with reference to the drawing.

The drawing is a schematic view illustrating an organic EL device 100 according to one or more embodiments of the present disclosure. The organic EL device 100 may include, for example, a substrate 102, an anode 104, a hole injection layer 106, a hole transport layer 108, an emission layer 110, an electron transport layer 112, an electron injection layer 114 and a cathode 116. In some embodiments, the material for an organic EL device according to embodiments of the present disclosure may be used in at least one layer selected from the stacked layers positioned between the emission layer and the anode.

For example, a case when the material for an organic EL device according to embodiments of the present disclosure is used in the hole transport layer 108 will be explained herein. The substrate 102 may be a transparent glass substrate, a semiconductor substrate formed using silicon, a flexible substrate of a resin, or the like. The anode 104 may be positioned on the substrate 102 and may be formed using indium tin oxide (ITO), indium zinc oxide (IZO), and/or the like. The hole injection layer 106 may be positioned on the anode 104 and may include, for example, 4,4',4''-tris(2-naphthyl(phenyl)amino)triphenylamine (2-TNATA), N,N,N',N'-tetrakis(3-methylphenyl)-3,3'-dimethylbenzidine (HMTPD), and/or the like. The hole transport layer 108 may be positioned on the hole injection layer 106 and may include the material for an organic EL device according to embodiments of the present disclosure. In some embodiments, the thickness of the hole transport layer 108 may be from about 3 nm to about 100 nm.

The emission layer 110 may be positioned on the hole transport layer 108, and may include a condensed polycyclic aromatic derivative selected from, for example, an anthracene derivative, a pyrene derivative, a fluoranthene derivative, a chrysene derivative, a benzoanthracene derivative and a triphenylene derivative. In some embodiments, the emission layer 110 may include the anthracene derivative or the pyrene derivative. The anthracene derivative used in the emission layer 110 may include a compound represented by the following General Formula (6):

General Formula (6)

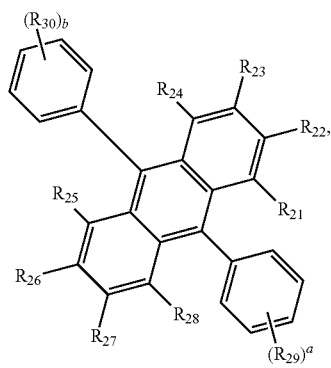

(6)

In the above General Formula (6), $R_{21}$ to $R_{30}$ may be each independently selected from a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a silyl group, a halogen atom, a hydrogen atom and a deuterium atom; "a" and "b" may be each independently an integer from 0 to 5; and adjacent groups selected from $R_{21}$ to $R_{30}$ may combine with each other (e.g., may be coupled to each other) to form a saturated or unsaturated ring.

The substituted or unsubstituted heteroaryl group having 1 to 30 carbon atoms for forming a ring used, for example, in $R_{21}$ to $R_{30}$ may include a benzothiazolyl group, a thiophenyl group, a thienothiophenyl group, a thienothienothiophenyl group, a benzothiophenyl group, a benzofuryl group, a dibenzothiophenyl group, an N-arylcarbazolyl group, an N-heteroarylcarbazolyl group, an N-alkylcarbazolyl group, a phenoxazyl group, a phenothiazyl group, a pyridyl group, a pyrimidyl group, a triazile group, a quinolinyl group, a quinoxalyl group, and/or the like, but is not limited thereto.

The alkyl group having 1 to 15 carbon atoms used, for example, in $R_{21}$ to $R_{30}$ may include a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, and/or the like, but is not limited thereto.

The anthracene derivative used in the emission layer 110 of the organic EL device according to embodiments of the present disclosure may include at least one compound selected from Compounds a-1 to a-6 illustrated below:

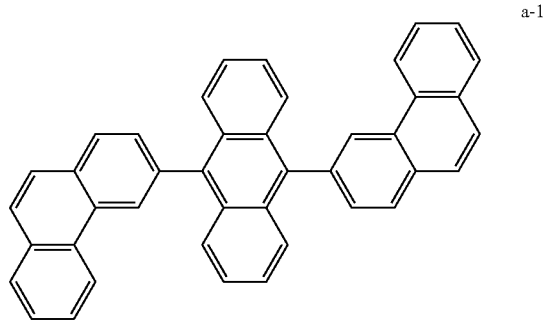

a-1

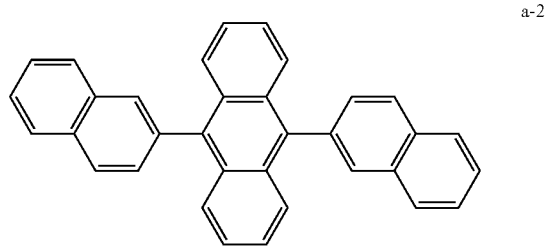

a-2 a-3
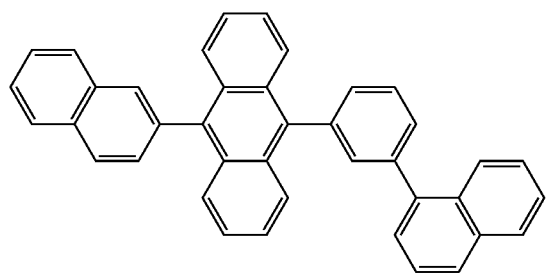
a-4
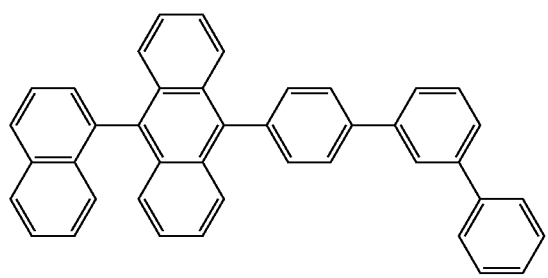
a-5
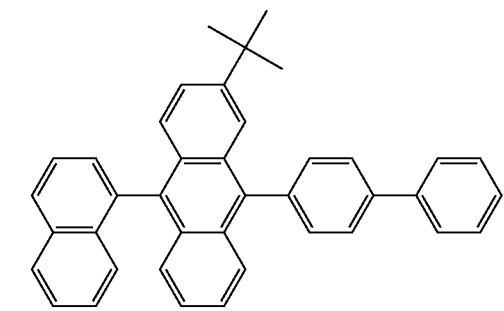
a-6
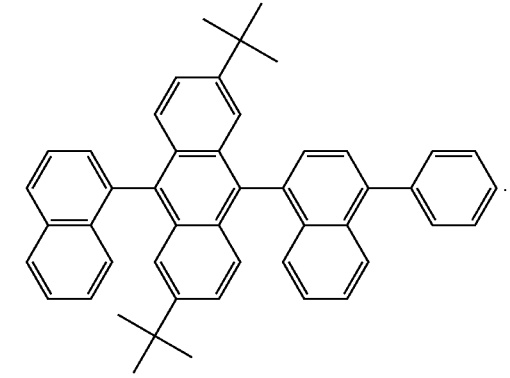
a-7
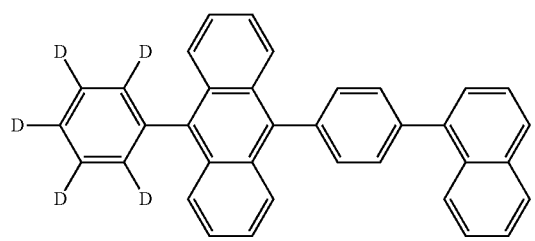
a-8
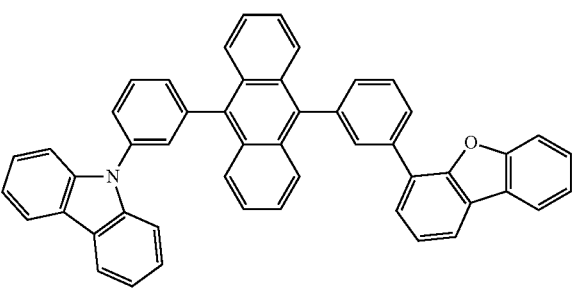
a-9
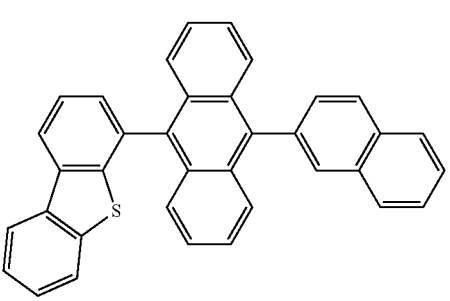
a-10
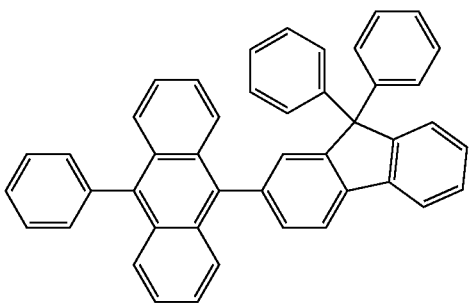
a-11
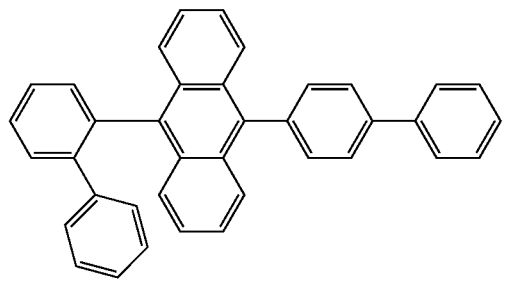
In some embodiments, the anthracene derivative used in the emission layer 110 of the organic EL device according to embodiments of the present disclosure may include at least one compound selected from Compounds a-7 to a-12 illustrated below:

-continued

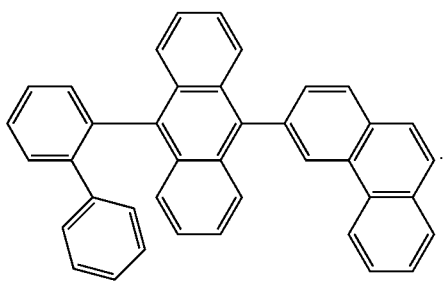

a-12

The emission layer 110 may include, for example, styryl derivatives (such as 1,4-bis[2-(3-N-ethylcarbazolyl)vinyl]benzene (BCzVB), 4-(di-p-tolylamino)-4'-[(di-p-tolylamino)styryl]stilbene (DPAVB), and/or N-(4-((E)-2-(6-((E)-4-(diphenylamino)styryl)naphthalene-2-yl)vinyl)phenyl)-N-phenylbenzeneamine (N-BDAVBI)), perylene and/or the derivatives thereof (such as 2,5,8,11-tetra-t-butylperylene (TBPe)), pyrene and/or the derivatives thereof (such as 1,1-dipyrene, 1,4-dipyrenylbenzene, and/or 1,4-bis(N,N-diphenylamino)pyrene), and/or the like, and a dopant included in the emission layer may be 2,5,8,11-tetra-t-butylperylene (TBP), and/or the like, but the composition of the emission layer is not limited thereto.

The electron transport layer 112 may be positioned on the emission layer 110 and may include, for example, tris(8-hydroxyquinolinato)aluminum (Alq3) and/or a material having a nitrogen-containing aromatic ring (for example, a material including a pyridine ring such as 1,3,5-tri[(3-pyridyl)-phen-3-yl]benzene, a material including a triazine ring such as 2,4,6-tris(3'-(pyridine-3-yl)biphenyl-3-yl)1,3,5-triazine, and/or a material including an imidazole derivative such as 2-(4-N-Phenylbenzoimidazolyl-1-ylphenyl)-9,10-dinaphthylanthracene).

The electron injection layer 114 may be positioned on the electron transport layer 112 and may include a material selected from, for example, lithium fluoride (LiF), lithium-8-quinolinato (Liq), and the like. The cathode 116 may be positioned on the electron injection layer 114 and may be formed using a metal (such as aluminum (Al), silver (Ag), lithium (Li), magnesium (Mg) and/or calcium (Ca)) or a transparent material (such as ITO and/or IZO). The above-described thin layers of the organic EL device may each be formed by selecting one or more suitable layer-forming methods according to the material for forming the layer and the kind of layer to be formed. Layer-forming methods may include, but are not limited to, a vacuum evaporation method, a sputtering method, various coating methods, and/or the like.

In the organic EL device 100 according to embodiments of the present disclosure, a hole transport layer including the material for an organic EL device according to embodiments of the present disclosure may exhibit low driving voltage, high emission efficiency and long life. The material for an organic EL device according to embodiments of the present disclosure may be applied (e.g., may be included) in an active matrix organic EL display using a thin film transistor (TFT).

According to embodiments of the present disclosure, an organic EL device driven at a low voltage and having high emission efficiency and long life may be manufactured by using the material for an organic EL device according to embodiments of the present disclosure in at least one layer selected from the stacked layers positioned between the emission layer and the anode.

EXAMPLES

Preparation Method

The material for an organic EL device according to embodiments of the present disclosure may be synthesized, for example, as follows. Hereinafter, a preparation method of Compound 7 will be described as an example. First, Compound A was synthesized as an intermediate as follows:

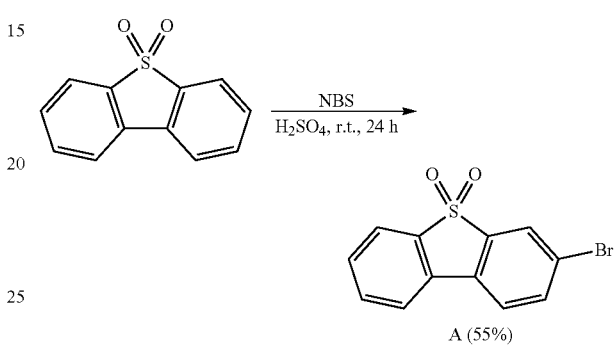

Under an argon atmosphere, 2.0 g of dibenzo[b,d]thiophene 5,5-dioxide, 60 mL of concentrated sulfuric acid and 3.29 g of N-bromosuccineimide (NBS) were added to a 500 mL flask, followed by stirring the resulting mixture at room temperature for about 24 hours. After stirring, the obtained reaction mixture was poured in cold water, precipitated solid was filtered with suction, and solvents were distilled. The crude product thus obtained was washed with water and methanol to produce Compound A as a white solid (2.0 g, Yield 55%). The molecular weight of Compound A measured by FAB-MS was 295.

Compound B was synthesized using Compound A as a raw material as follows:

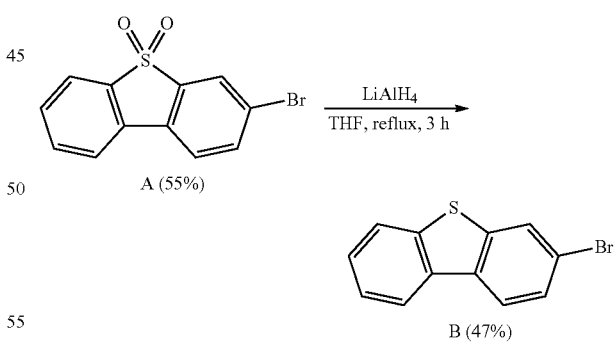

Under an argon atmosphere, 10.1 g of Compound A and 1.3 g of lithium aluminum hydride (LiAlH$_4$) were added to a 500 mL flask, followed by heating and refluxing the resulting mixture in 174 mL of a tetrahydrofuran (THF) solvent for about 3 hours. After air cooling, the obtained reaction mixture was extracted with ethyl acetate, and magnesium sulfate (Mg$_2$SO$_4$) and activated clay were added to the extract. Then, the extract was filtered with suction, and solvents were distilled. The crude product thus obtained was separated by silica gel column chromatography using a mixture solvent of dichloromethane and hexane to produce Compound B as a pale yellow solid (4.23 g, Yield 47%). The molecular weight of Compound B measured by FAB-MS was 263.

Compound 7 was synthesized using Compound B as a raw material as follows:

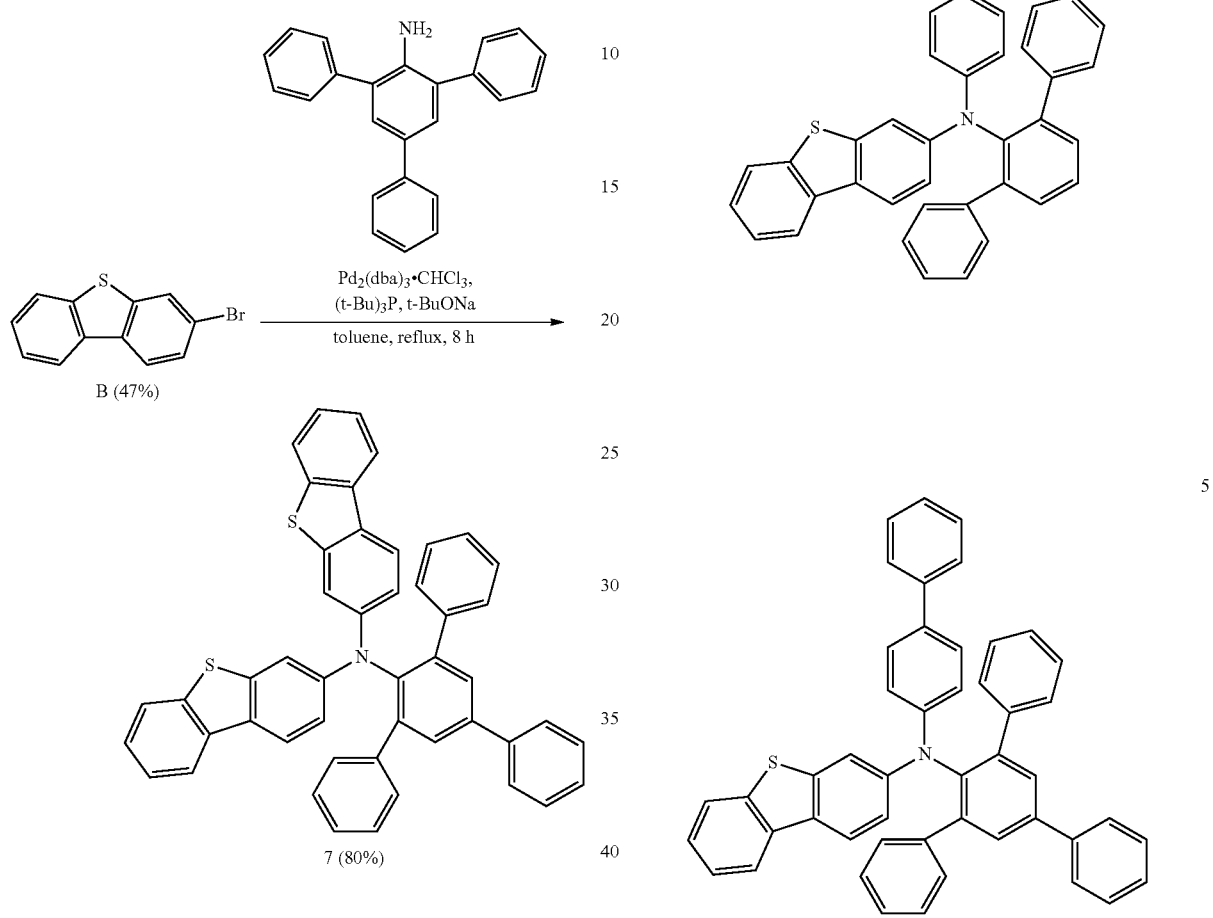

Under an argon atmosphere, 1.50 g of Compound B, 0.900 g of 5'-phenyl-[1,1':3',1''-terphenyl]-2'-amine, 0.340 g of tris(dibenzylideneacetone)dipalladium(O) (Pd$_2$(dba)$_3$) chloroform adduct, 0.150 g of tri-tert-butylphosphine ((t-Bu)$_3$P) and 1.35 g of sodium tert-butoxide were added to a 500 mL, three-necked flask, followed by heating and stirring the resulting mixture in a xylene solvent at about 120° C. for about 10 hours. After air cooling, water was added thereto, and an organic layer was separated. Activated carbon was added to the obtained organic layer, hot filtration was performed, and solvents were distilled. Recrystallization was performed using a mixture solvent of THF and hexane to produce Compound 7 as a pale yellow solid (1.54 g, Yield 80%).

The molecular weight of Compound 7 measured by FAB-MS was 686. The chemical shift values of Compound 7 measured by $^1$H-NMR (CDCl$_3$) were 8.45 (d, 2H, J=7.82 Hz), 7.98 (d, 2H, J=7.80 Hz), 7.80 (d, 2H, J=7.60 Hz), 7.55-7.50 (m, 12H), 7.42-7.39 (m, 5H), 7.08-7.01 (m, 6H), 6.89-6.80 (m, 2H).

Organic EL devices according to Examples 1 to 8 were each manufactured by substantially the same method as the above-described manufacturing method, and respectively using Compounds 1, 5, 6, 7, 17, 41, 65 and 81 as hole transport materials.

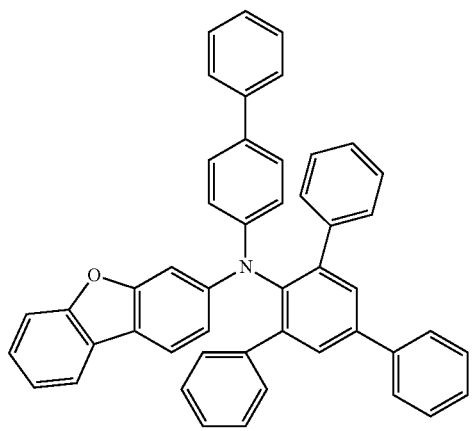

7
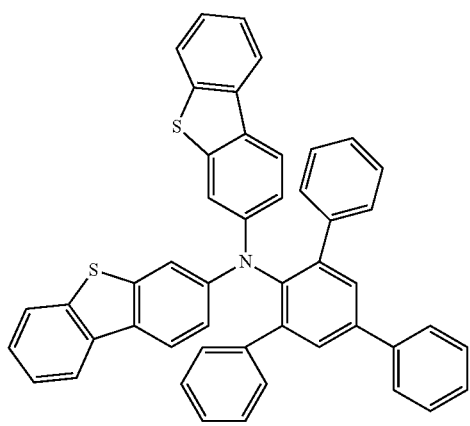
17
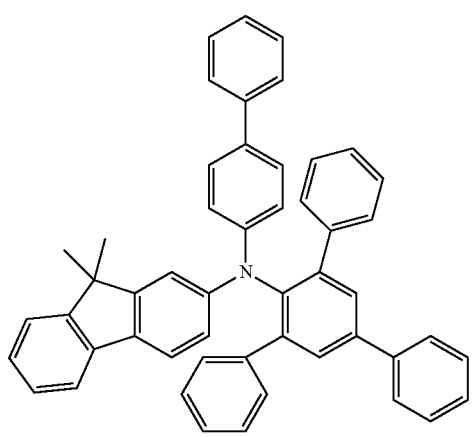
41
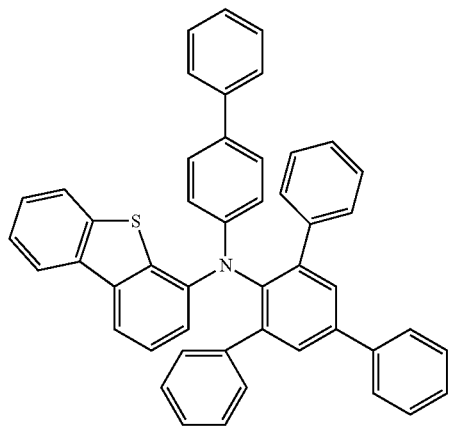
65
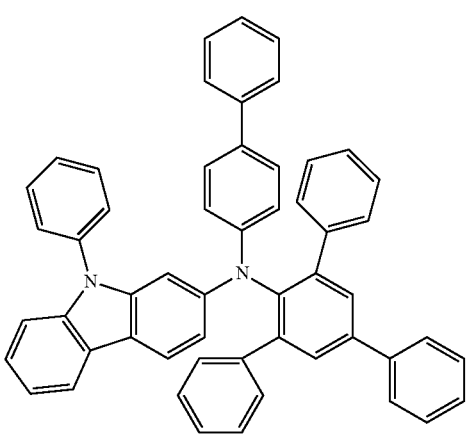
81
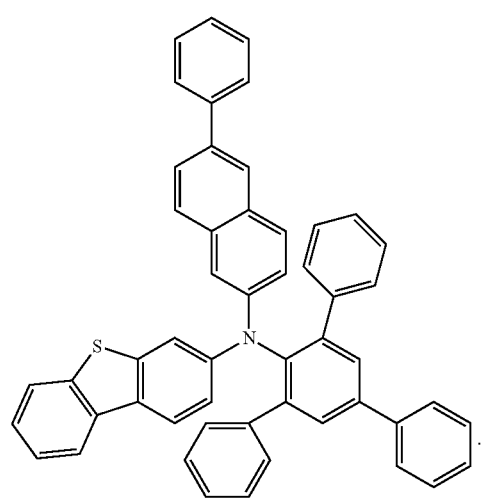
In addition, organic EL devices according to Comparative Examples 1 to 3 were each manufactured by substantially the same method as the above-described manufacturing method, and respectively using Compounds 85 to 87 (illustrated below) as hole transport materials.
85
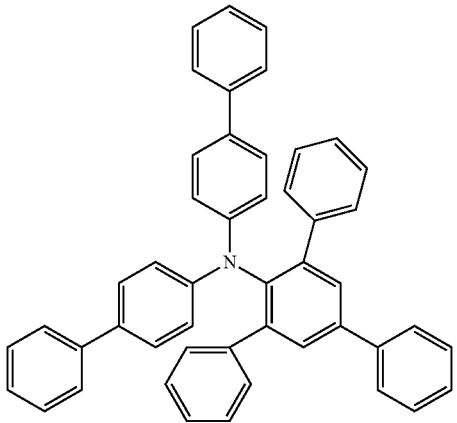

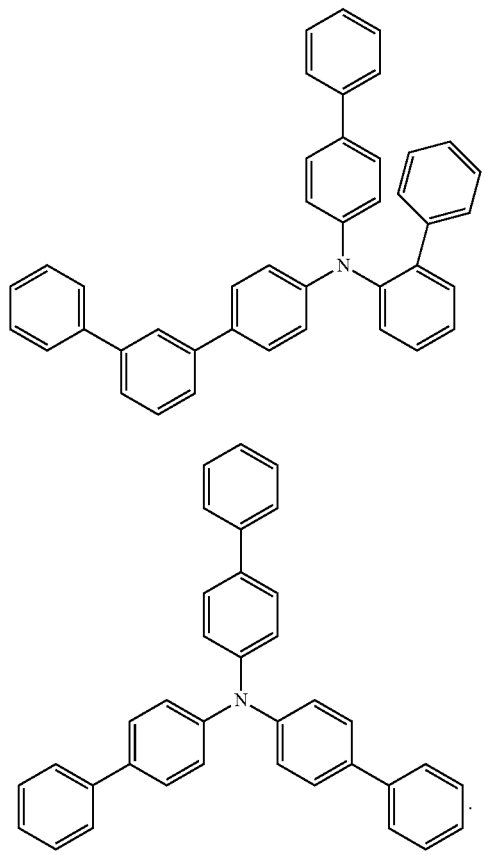

In the organic EL devices of Examples 1 to 8 and Comparative Examples 1 to 3, a transparent glass substrate was used as a substrate 102, an anode 104 was formed using ITO to a layer thickness of about 150 nm, a hole injection layer 106 was formed using 2-TNATA to a layer thickness of about 60 nm, a hole transport layer 108 was formed using the respective compounds to a layer thickness of about 30 nm, an emission layer 110 was formed using ADN doped with 3% TBP to a layer thickness of about 25 nm, an electron transport layer 112 was formed using Alq3 to a layer thickness of about 25 nm, an electron injection layer 114 was formed using LiF to a layer thickness of about 1 nm, and a cathode 116 was formed using Al to a layer thickness of about 100 nm.

For each of the organic EL devices of Examples 1 to 8 and Comparative Examples 1 to 3, voltage and emission efficiency were evaluated and the results are shown in Table 1. The evaluation was performed with current density of about 10 mA/cm$^2$. In Table 1, "Life LT50" indicates half-life and refers to the time (in hours) that it took for the initial luminance of the organic EL device to decrease to 50%.

TABLE 1

| Example of manufacturing device | Hole transport layer | Voltage (V) | Emission efficiency (cd/A) | Life LT50 (h) |
| --- | --- | --- | --- | --- |
| Example 1 | Compound 1 | 5.6 | 6.7 | 2,000 |
| Example 2 | Compound 5 | 5.6 | 6.7 | 2,200 |
| Example 3 | Compound 6 | 6.0 | 6.5 | 2,050 |
| Example 4 | Compound 7 | 5.7 | 6.6 | 2,100 |
| Example 5 | Compound 17 | 6.0 | 6.5 | 1,950 |
| Example 6 | Compound 41 | 6.2 | 6.5 | 1,850 |
| Example 7 | Compound 65 | 6.0 | 6.6 | 1,950 |
| Example 8 | Compound 81 | 6.2 | 6.5 | 1,950 |
| Comparative Example 1 | Comparative Compound 85 | 6.3 | 5.3 | 1,400 |
| Comparative Example 2 | Comparative Compound 86 | 6.5 | 5.4 | 1,250 |
| Comparative Example 3 | Comparative Compound 87 | 6.6 | 5.0 | 1,200 |

From the results shown in Table 1, the organic EL devices according to Examples 1 to 8 that used the material for an organic EL device according to embodiments of the present disclosure, in which a dibenzoheterole part or a fluorene part is coupled with [1,1':3',1''-terphenyl]-2'-amino group, in the hole transport layer were driven at a lower voltage and had higher emission efficiency and longer life when compared to the organic EL devices according to Comparative Examples 1 to 3. Without being bound by any particular theory, it is believed that these improved results were obtained because the materials for an organic EL device used in Examples 1 to 8 had improved amorphous properties while maintaining amine properties.

In addition, in the organic EL device according to Example 2 using Compound 5 in which $R_2$ in General Formula (1) was a phenyl group, amorphous properties were improved, and the resulting organic EL device exhibited long life.

The material for an organic EL device according to embodiments of the present disclosure, in which a dibenzoheterole part or a fluorene part is coupled with [1,1':3',1''-terphenyl]-2'-amino group and the planarity of the molecule may be broken, amine properties may be maintained and amorphous properties may be improved. When such material is used for the manufacture of the organic EL device, low driving voltage, high emission efficiency and long life may be realized. For example, improved properties of the organic EL device may be obtained in a blue emission region.

The material for an organic EL device according to embodiments of the present disclosure may realize an organic EL device driven at a low voltage and having high emission efficiency and long life. For example, the material for an organic EL device according to the present disclosure may be included in at least one layer selected from the stacked layers positioned between an emission layer and an anode and may realize an organic EL device driven at a low voltage and having high emission efficiency and long life in a blue emission layer. In embodiments of the present disclosure, high emission efficiency and long life of an organic EL device may be realized by introducing a material having a dibenzoheterole part or a fluorene part coupled with [1,1':3',1''-terphenyl]-2-amino group. When such [1,1':3',1''-terphenyl]-2'-amine derivative (having long life) is used as a hole transport material, amine properties may be maintained, amorphous properties may be improved, and high emission efficiency and long life of the resulting organic EL device may be realized.

As used herein, expressions such as "at least one selected from" and "one selected from," when preceding a list of elements, modify the entire list of elements and do not modify the individual elements of the list. Further, the use of "may" when describing embodiments of the present invention refers to "one or more embodiments of the present invention."

In addition, as used herein, the terms "use," "using," and "used" may be considered synonymous with the terms "utilize," "utilizing," and "utilized," respectively. Also, the term "substantially," "about," and similar terms are used as terms of approximation and not as terms of degree, and are intended to account for the inherent deviations in measured or calculated values that would be recognized by those of ordinary skill in the art.

In addition, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. § 112(a) and 35 U.S.C. § 132(a).

The above-disclosed subject matter is to be considered illustrative and not restrictive, and the appended claims and equivalents thereof are intended to cover all such modifications, enhancements, and other embodiments, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing description.

What is claimed is:

1. An organic electroluminescent (EL) device, comprising:
    an anode;
    a cathode;
    an emission layer between the anode and the cathode; and
    a plurality of layers between the emission layer and the anode, at least one layer selected from the plurality of layers comprising a material for an organic EL device,
    wherein the plurality of layers comprises a hole injection layer and one hole transport layer, and
    wherein the material is represented by General Formula (1):

General Formula (1)

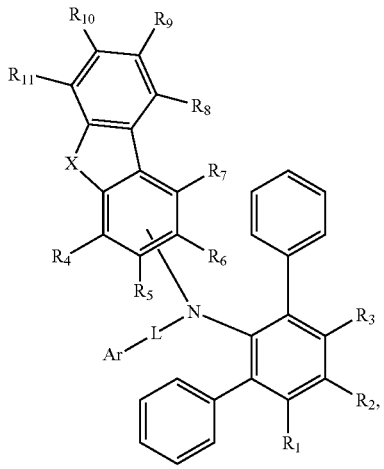

wherein in General Formula (1),
X is selected from $CR_{12}R_{13}$ and $SiR_{14}R_{15}$,
$R_1$ to $R_{16}$ are each independently selected from a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a silyl group, a halogen atom, a hydrogen atom and a deuterium atom,
L is selected from a direct linkage, a substituted or unsubstituted arylene group having 6 to 30 carbon atoms for forming a ring, a substituted or unsubstituted heteroarylene group having 1 to 30 carbon atoms for forming a ring and a divalent silyl group, and
Ar is selected from an unsubstituted aryl group having 6 to 14 carbon atoms for forming a ring or an aryl group having 6 to 14 carbon atoms for forming a ring substituted with an aryl group having 6 to 14 carbon atoms for forming a ring.

2. The organic EL device of claim 1, wherein in General Formula (1), $R_2$ is a phenyl group, and the material is represented by General Formula (2):

General Formula (2)

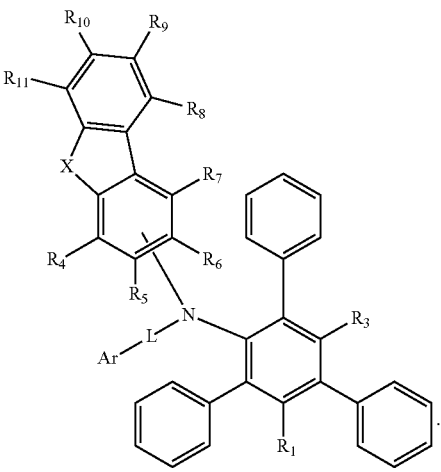

3. The organic EL device of claim 1, wherein in General Formula (1), $R_1$ and $R_3$ are each independently selected from a hydrogen atom and a deuterium atom, $R_2$ is a phenyl group, and $R_5$ forms a direct linkage with N, and the material is represented by General Formula (3):

General Formula (3)

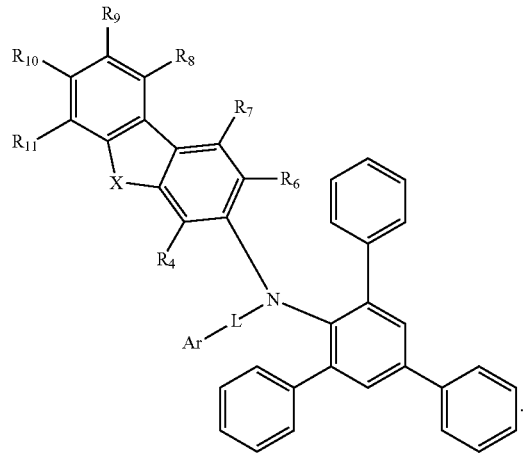
(3)

4. The organic EL device of claim 1, wherein a plurality of adjacent groups selected from $R_1$ to $R_{16}$ are coupled to each other to form a saturated or unsaturated ring.

5. The organic EL device of claim 1, wherein in General Formula (1), when X is selected from $CR_{12}R_{13}$ and $SiR_{14}R_{15}$, $R_5$ is coupled at position 2 as shown in General Formula (5):

General Formula (5)

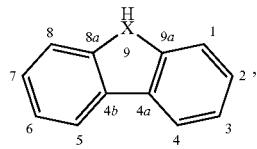
(5)

wherein in General Formula (5), H represents one or more substituents of X.

6. The organic EL device of claim 1, wherein the material for an organic EL device comprises at least one selected from Compounds 13 to 18 and 21 to 24:

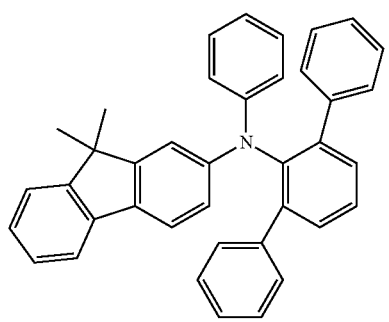
13

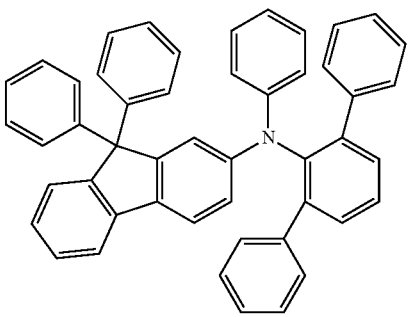
14

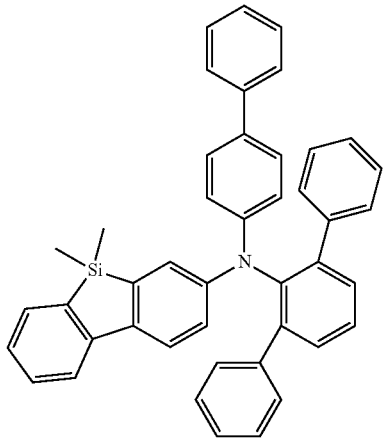
15

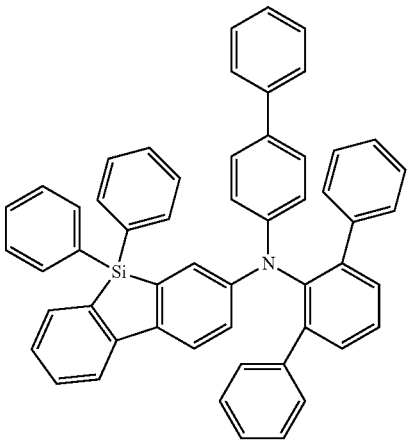
16

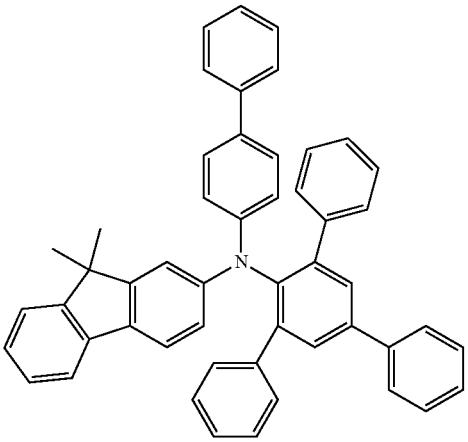
17

18
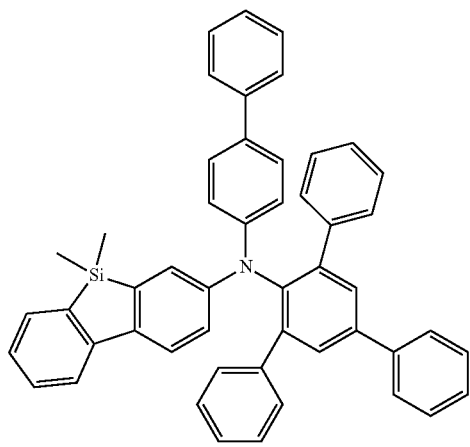
23
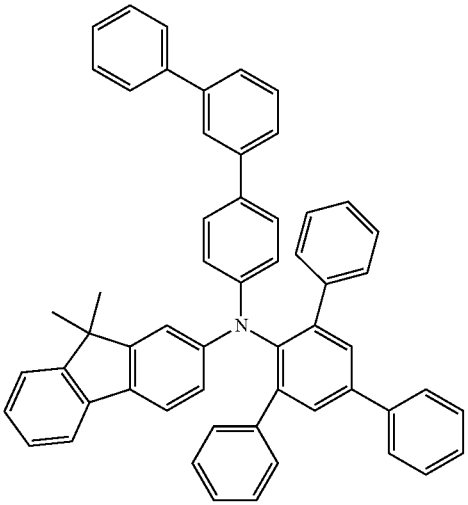
21 20
24
25
30
35
40
22 45
7. The organic EL device of claim 1, wherein the emission layer comprises an anthracene derivative or a pyrene derivative.
8. The organic EL device of claim 1, wherein the emission layer comprises a compound represented by General Formula (6):
General Formula (6)
(6)
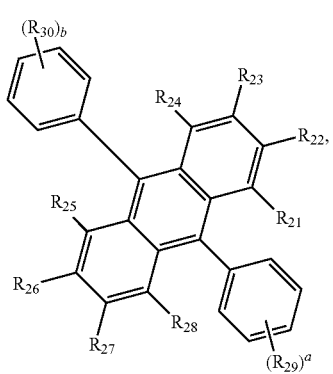
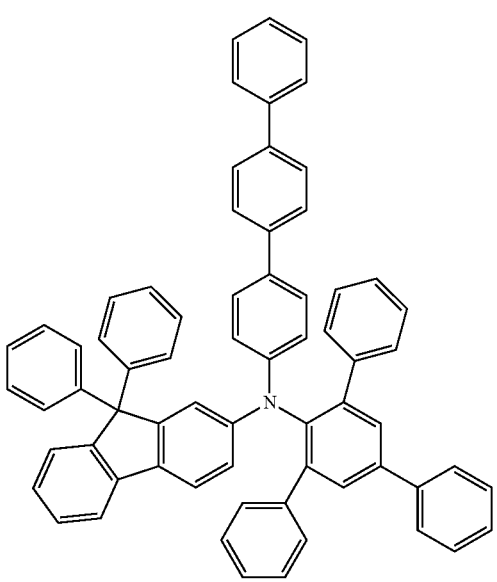

wherein in General Formula (6), $R_{21}$ to $R_{30}$ are each independently selected from a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a silyl group, a halogen atom, a hydrogen atom and a deuterium atom, "a" and "b" are each independently an integer from 0 to 5, and a plurality of adjacent groups selected from $R_{21}$ to $R_{30}$ are coupled to each other to form a saturated or unsaturated ring.

9. The organic EL device of claim 1, wherein the emission layer comprises at least one compound selected from Compounds a-1 to a-12:

a-1
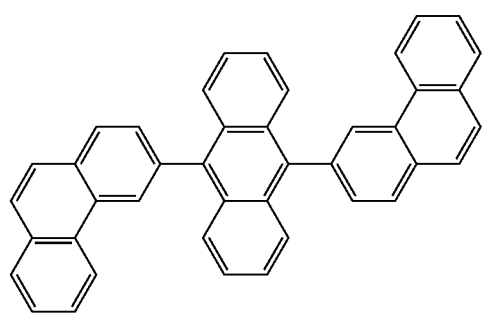

a-2
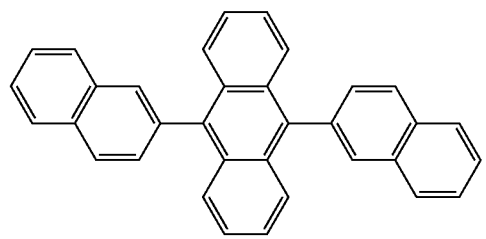

a-3
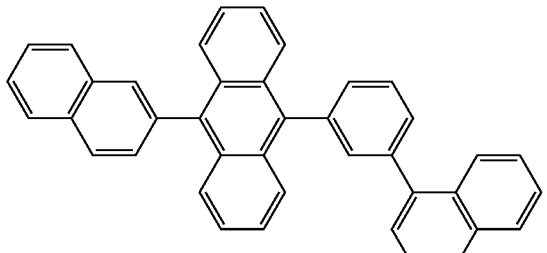

a-4
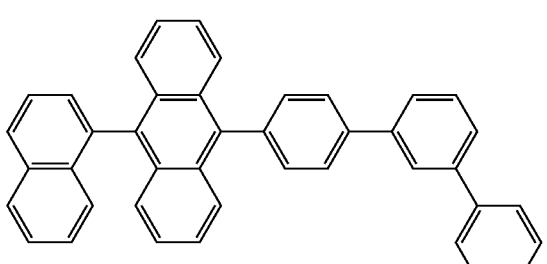

a-5
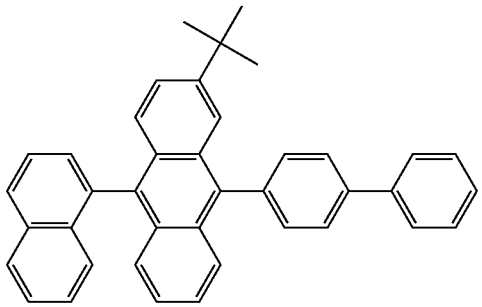

a-6
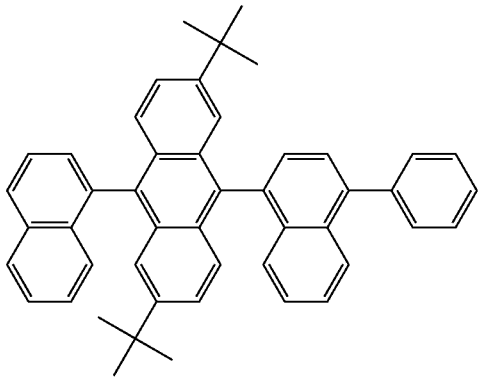

a-7
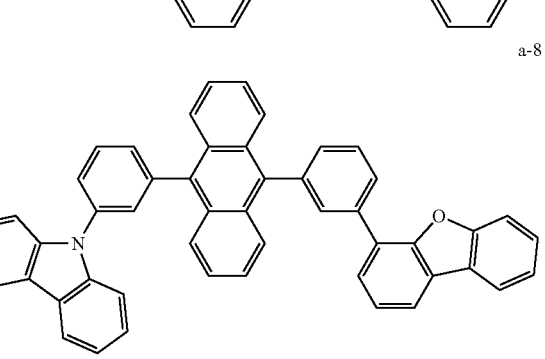

a-8
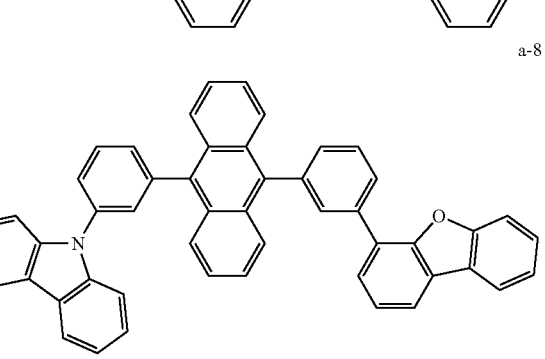

a-9
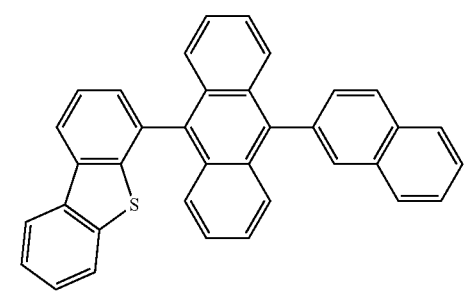

a-10
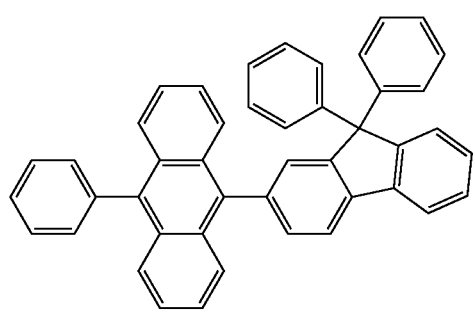
a-11
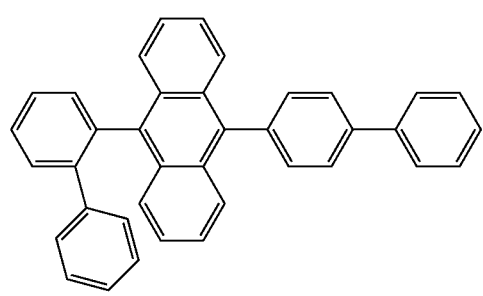
a-12
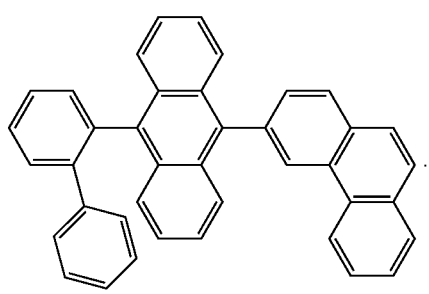
10. A material for an organic electroluminescent (EL) device is at least one selected from Compounds 13 to 24:
13
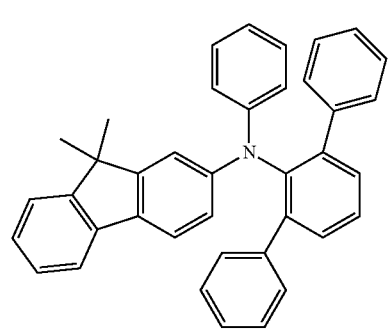
14
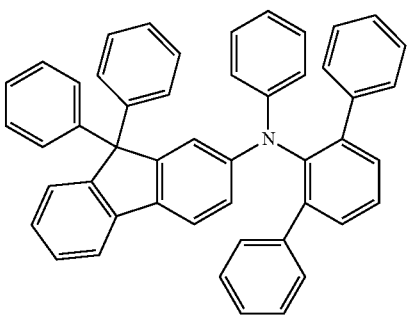
15
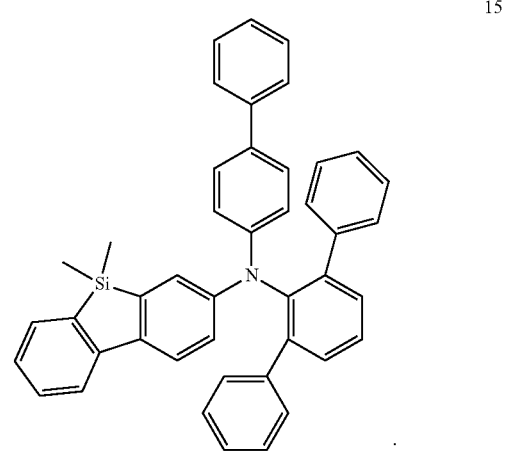
16
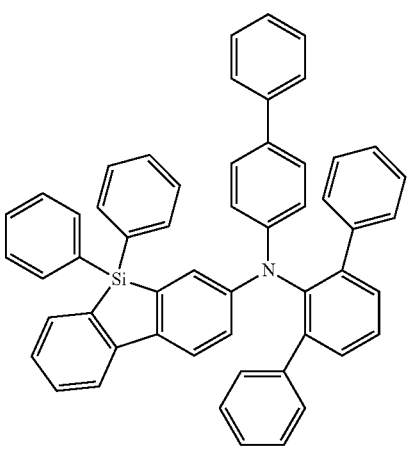
17
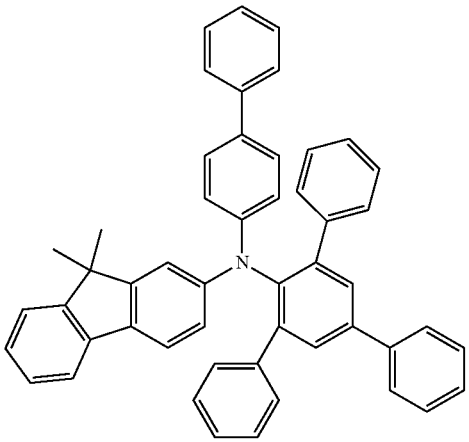

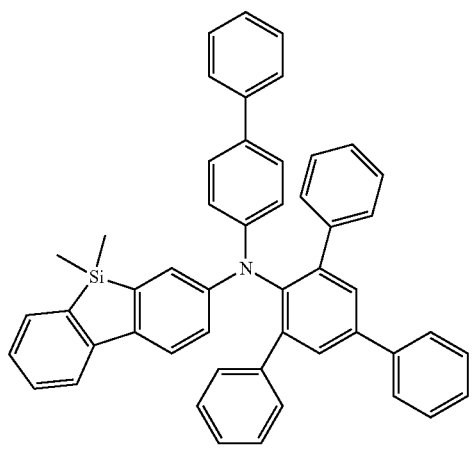
18
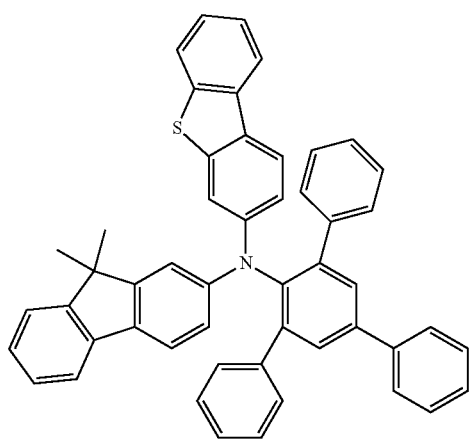
19
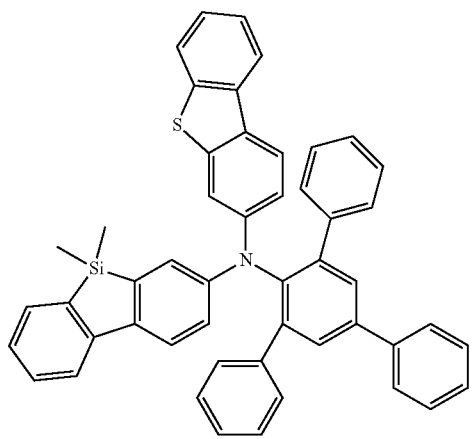
20
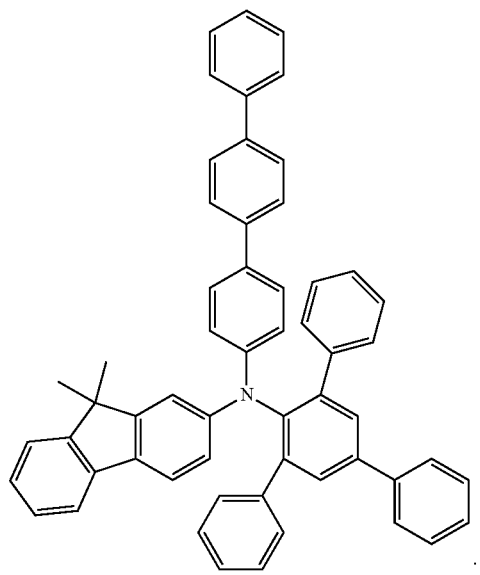
21
22
23

24
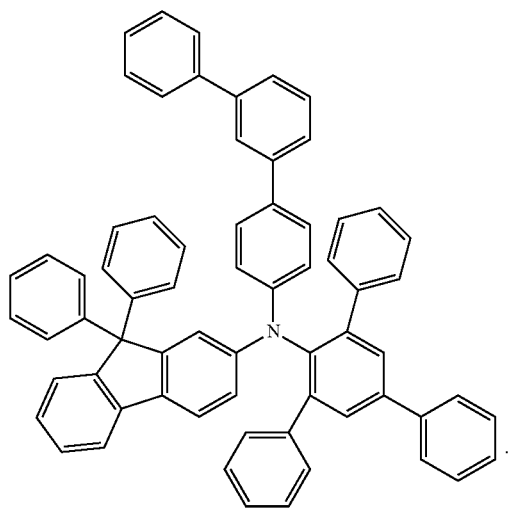
* * * * *